United States Patent
Sgroi, Jr.

(10) Patent No.: US 11,141,162 B2
(45) Date of Patent: Oct. 12, 2021

(54) LOADING UNIT LOCKING COLLAR WITH LINEARLY ACTUATED RELEASE

(71) Applicant: Covidien LP, Mansfield, MA (US)

(72) Inventor: Anthony Sgroi, Jr., Wallingford, CT (US)

(73) Assignee: Covidien LP, Mansfield, MA (US)

( * ) Notice: Subject to any disclaimer, the term of this patent is extended or adjusted under 35 U.S.C. 154(b) by 1151 days.

(21) Appl. No.: 15/205,169

(22) Filed: Jul. 8, 2016

(65) Prior Publication Data
US 2018/0008272 A1 Jan. 11, 2018

(51) Int. Cl.
*A61B 17/115* (2006.01)
*A61B 17/072* (2006.01)
*A61B 17/00* (2006.01)
*A61B 90/00* (2016.01)

(52) U.S. Cl.
CPC ........ *A61B 17/1155* (2013.01); *A61B 17/072* (2013.01); *A61B 2017/0046* (2013.01); *A61B 2017/0053* (2013.01); *A61B 2017/00473* (2013.01); *A61B 2017/00477* (2013.01); *A61B 2017/07271* (2013.01); *A61B 2090/0811* (2016.02)

(58) Field of Classification Search
CPC ...... A61B 2017/07271; A61B 17/1155; A61B 17/072; A61B 2090/0811; A61B 2017/0046; A61B 2017/00473; A61B 2017/00477; A61B 2017/0053
USPC ..................................................... 227/175.1
See application file for complete search history.

(56) References Cited

U.S. PATENT DOCUMENTS

| | | |
|---|---|---|
| 3,193,165 A | 7/1965 | Akhalaya et al. |
| 3,388,847 A | 6/1968 | Kasulin et al. |
| 3,552,626 A | 1/1971 | Astafiev et al. |
| (Continued) | | |

FOREIGN PATENT DOCUMENTS

| | | |
|---|---|---|
| CA | 908529 A | 8/1972 |
| CN | 201481477 U | 5/2010 |
| (Continued) | | |

OTHER PUBLICATIONS

European Search Report dated Sep. 1, 2016, issued in EP 16166326.
(Continued)

*Primary Examiner* — Thanh K Truong
*Assistant Examiner* — David G Shutty

(57) ABSTRACT

A loading unit includes a shell assembly, a lock collar, and a release collar. The shell assembly has a coupling ring that defines a lock slot and a proximal opening configured to receive a distal end portion of a surgical instrument. The lock collar is disposed about the coupling ring and has a radially extending lock that is configured to be received within the lock slot. The lock collar is transitionable between a locked configuration in which the lock is positioned within the lock slot and an unlocked configuration in which the lock is lifted from within the lock slot. The release collar is disposed about the coupling ring proximal of the lock collar and is transitionable between an unactuated position and an actuated position. The release collar transitioning the lock collar to the unlocked configuration as the release collar is translated from the unactutated position towards the actuated position.

20 Claims, 15 Drawing Sheets

(56) References Cited

U.S. PATENT DOCUMENTS

| | | | |
|---|---|---|---|
| 3,638,652 A | 2/1972 | Kelley | |
| 3,771,526 A | 11/1973 | Rudie | |
| 4,198,982 A | 4/1980 | Fortner et al. | |
| 4,207,898 A | 6/1980 | Becht | |
| 4,289,133 A | 9/1981 | Rothfuss | |
| 4,304,236 A | 12/1981 | Conta et al. | |
| 4,319,576 A | 3/1982 | Rothfuss | |
| 4,350,160 A | 9/1982 | Kolesov et al. | |
| 4,351,466 A | 9/1982 | Noiles | |
| 4,379,457 A | 4/1983 | Gravener et al. | |
| 4,473,077 A | 9/1984 | Noiles et al. | |
| 4,476,863 A | 10/1984 | Kanshin et al. | |
| 4,485,817 A | 12/1984 | Swiggett | |
| 4,488,523 A | 12/1984 | Shichman | |
| 4,505,272 A | 3/1985 | Utyamyshev et al. | |
| 4,505,414 A | 3/1985 | Filipi | |
| 4,520,817 A | 6/1985 | Green | |
| 4,550,870 A | 11/1985 | Krumme et al. | |
| 4,573,468 A | 3/1986 | Conta et al. | |
| 4,576,167 A | 3/1986 | Noiles | |
| 4,592,354 A | 6/1986 | Rothfuss | |
| 4,603,693 A | 8/1986 | Conta et al. | |
| 4,606,343 A | 8/1986 | Conta et al. | |
| 4,632,290 A | 12/1986 | Green et al. | |
| 4,646,745 A | 3/1987 | Noiles | |
| 4,665,917 A | 5/1987 | Clanton et al. | |
| 4,667,673 A | 5/1987 | Li | |
| 4,671,445 A | 6/1987 | Barker et al. | |
| 4,700,703 A | 10/1987 | Resnick et al. | |
| 4,703,887 A | 11/1987 | Clanton et al. | |
| 4,708,141 A | 11/1987 | Inoue et al. | |
| 4,717,063 A | 1/1988 | Ebihara | |
| 4,752,024 A | 6/1988 | Green et al. | |
| 4,754,909 A | 7/1988 | Barker et al. | |
| 4,776,506 A | 10/1988 | Green | |
| 4,817,847 A | 4/1989 | Redtenbacher et al. | |
| 4,873,977 A | 10/1989 | Avant et al. | |
| 4,893,662 A | 1/1990 | Gervasi | |
| 4,903,697 A | 2/1990 | Resnick et al. | |
| 4,907,591 A | 3/1990 | Vasconcellos et al. | |
| 4,917,114 A | 4/1990 | Green et al. | |
| 4,957,499 A | 9/1990 | Lipatov et al. | |
| 4,962,877 A | 10/1990 | Hervas | |
| 5,005,749 A | 4/1991 | Aranyi | |
| 5,042,707 A | 8/1991 | Taheri | |
| 5,047,039 A | 9/1991 | Avant et al. | |
| 5,104,025 A | 4/1992 | Main et al. | |
| 5,119,983 A | 6/1992 | Green et al. | |
| 5,122,156 A | 6/1992 | Granger et al. | |
| 5,139,513 A | 8/1992 | Segato | |
| 5,158,222 A | 10/1992 | Green et al. | |
| 5,188,638 A | 2/1993 | Tzakis | |
| 5,193,731 A | 3/1993 | Aranyi | |
| 5,197,648 A | 3/1993 | Gingold | |
| 5,197,649 A | 3/1993 | Bessler et al. | |
| 5,205,459 A | 4/1993 | Brinkerhoff et al. | |
| 5,221,036 A | 6/1993 | Takase | |
| 5,222,963 A | 6/1993 | Brinkerhoff et al. | |
| 5,253,793 A | 10/1993 | Green et al. | |
| 5,261,920 A | 11/1993 | Main et al. | |
| 5,265,343 A * | 11/1993 | Pascaloff | B23D 51/10 30/339 |
| 5,271,543 A | 12/1993 | Grant et al. | |
| 5,271,544 A | 12/1993 | Fox et al. | |
| 5,275,322 A | 1/1994 | Brinkerhoff et al. | |
| 5,275,443 A * | 1/1994 | Klinger | F16L 37/144 285/305 |
| 5,282,810 A | 2/1994 | Allen et al. | |
| 5,285,944 A | 2/1994 | Green et al. | |
| 5,285,945 A | 2/1994 | Brinkerhoff et al. | |
| 5,292,053 A | 3/1994 | Bilotti et al. | |
| 5,309,927 A | 5/1994 | Welch | |
| 5,312,024 A | 5/1994 | Grant et al. | |
| 5,314,435 A | 5/1994 | Green et al. | |
| 5,314,436 A | 5/1994 | Wilk | |
| 5,330,486 A | 7/1994 | Wilk | |
| 5,333,773 A | 8/1994 | Main | |
| 5,344,059 A | 9/1994 | Green et al. | |
| 5,346,115 A | 9/1994 | Perouse et al. | |
| 5,348,259 A | 9/1994 | Blanco et al. | |
| 5,350,104 A | 9/1994 | Main et al. | |
| 5,355,897 A | 10/1994 | Pietrafitta et al. | |
| 5,360,154 A | 11/1994 | Green | |
| 5,368,215 A | 11/1994 | Green et al. | |
| 5,392,979 A | 2/1995 | Green et al. | |
| 5,395,030 A | 3/1995 | Kuramoto et al. | |
| 5,403,333 A | 4/1995 | Kaster et al. | |
| 5,404,870 A | 4/1995 | Brinkerhoff et al. | |
| 5,411,508 A | 5/1995 | Bessler et al. | |
| 5,425,738 A | 6/1995 | Gustafson et al. | |
| 5,433,721 A | 7/1995 | Hooven et al. | |
| 5,437,684 A | 8/1995 | Calabrese et al. | |
| 5,439,156 A | 8/1995 | Grant et al. | |
| 5,443,198 A | 8/1995 | Viola et al. | |
| 5,447,514 A | 9/1995 | Gerry et al. | |
| 5,454,825 A | 10/1995 | Van Leeuwen et al. | |
| 5,464,415 A | 11/1995 | Chen | |
| 5,470,006 A | 11/1995 | Rodak | |
| 5,474,223 A | 12/1995 | Viola et al. | |
| 5,497,934 A | 3/1996 | Brady et al. | |
| 5,503,635 A | 4/1996 | Sauer et al. | |
| 5,522,534 A | 6/1996 | Viola et al. | |
| 5,533,661 A | 7/1996 | Main et al. | |
| 5,588,579 A | 12/1996 | Schnut et al. | |
| 5,609,285 A | 3/1997 | Grant et al. | |
| 5,626,591 A | 5/1997 | Kockerling et al. | |
| 5,632,433 A | 5/1997 | Grant et al. | |
| 5,639,008 A | 6/1997 | Gallagher et al. | |
| 5,641,111 A | 6/1997 | Ahrens et al. | |
| 5,658,300 A | 8/1997 | Bito et al. | |
| 5,669,918 A | 9/1997 | Balazs et al. | |
| 5,685,474 A | 11/1997 | Seeber | |
| 5,709,335 A | 1/1998 | Heck | |
| 5,715,987 A | 2/1998 | Kelley et al. | |
| 5,718,360 A | 2/1998 | Green et al. | |
| 5,720,755 A | 2/1998 | Dakov | |
| 5,732,872 A | 3/1998 | Bolduc et al. | |
| 5,749,896 A | 5/1998 | Cook | |
| 5,758,814 A | 6/1998 | Gallagher et al. | |
| 5,799,857 A | 9/1998 | Robertson et al. | |
| 5,814,055 A | 9/1998 | Knodel et al. | |
| 5,833,698 A | 11/1998 | Hinchliffe et al. | |
| 5,836,503 A | 11/1998 | Ehrenfels et al. | |
| 5,839,639 A | 11/1998 | Sauer et al. | |
| 5,855,312 A | 1/1999 | Toledano | |
| 5,860,581 A | 1/1999 | Robertson et al. | |
| 5,868,760 A | 2/1999 | McGuckin, Jr. | |
| 5,881,943 A | 3/1999 | Heck et al. | |
| 5,888,200 A * | 3/1999 | Walen | A61B 17/1622 606/167 |
| 5,915,616 A | 6/1999 | Viola et al. | |
| 5,947,363 A | 9/1999 | Bolduc et al. | |
| 5,951,576 A | 9/1999 | Wakabayashi | |
| 5,957,363 A | 9/1999 | Heck | |
| 5,993,468 A | 11/1999 | Rygaard | |
| 6,024,748 A | 2/2000 | Manzo et al. | |
| 6,050,472 A | 4/2000 | Shibata | |
| 6,053,390 A | 4/2000 | Green et al. | |
| 6,068,636 A | 5/2000 | Chen | |
| 6,083,241 A | 7/2000 | Longo et al. | |
| 6,102,271 A | 8/2000 | Longo et al. | |
| 6,117,148 A | 9/2000 | Ravo et al. | |
| 6,119,913 A | 9/2000 | Adams et al. | |
| 6,126,058 A | 10/2000 | Adams et al. | |
| 6,142,933 A | 11/2000 | Longo et al. | |
| 6,149,667 A | 11/2000 | Hovland et al. | |
| 6,176,413 B1 | 1/2001 | Heck et al. | |
| 6,179,195 B1 | 1/2001 | Adams et al. | |
| 6,193,129 B1 | 2/2001 | Bittner et al. | |
| 6,203,553 B1 | 3/2001 | Robertson et al. | |
| 6,209,773 B1 | 4/2001 | Bolduc et al. | |
| 6,241,140 B1 | 6/2001 | Adams et al. | |
| 6,253,984 B1 | 7/2001 | Heck et al. | |
| 6,258,107 B1 | 7/2001 | Balazs et al. | |

(56) References Cited

U.S. PATENT DOCUMENTS

| | | | |
|---|---|---|---|
| 6,264,086 | B1 | 7/2001 | McGuckin, Jr. |
| 6,269,997 | B1 | 8/2001 | Balazs et al. |
| 6,273,897 | B1 | 8/2001 | Dalessandro et al. |
| 6,279,809 | B1 | 8/2001 | Nicolo |
| 6,302,311 | B1 | 10/2001 | Adams et al. |
| 6,338,737 | B1 | 1/2002 | Toledano |
| 6,343,731 | B1 | 2/2002 | Adams et al. |
| 6,387,105 | B1 | 5/2002 | Gifford, III et al. |
| 6,398,795 | B1 | 6/2002 | McAlister et al. |
| 6,402,008 | B1 | 6/2002 | Lucas |
| 6,439,446 | B1 | 8/2002 | Perry et al. |
| 6,443,973 | B1 | 9/2002 | Whitman |
| 6,450,390 | B2 | 9/2002 | Heck et al. |
| 6,478,210 | B2 | 11/2002 | Adams et al. |
| 6,488,197 | B1 | 12/2002 | Whitman |
| 6,491,201 | B1 | 12/2002 | Whitman |
| 6,494,877 | B2 | 12/2002 | Odell et al. |
| 6,503,259 | B2 | 1/2003 | Huxel et al. |
| 6,517,566 | B1 | 2/2003 | Hovland et al. |
| 6,520,398 | B2 | 2/2003 | Nicolo |
| 6,533,157 | B1 | 3/2003 | Whitman |
| 6,551,334 | B2 | 4/2003 | Blatter et al. |
| 6,578,751 | B2 | 6/2003 | Hartwick |
| 6,585,144 | B2 | 7/2003 | Adams et al. |
| 6,588,643 | B2 | 7/2003 | Bolduc et al. |
| 6,592,596 | B1 | 7/2003 | Geitz |
| 6,601,749 | B2 | 8/2003 | Sullivan et al. |
| 6,605,078 | B2 | 8/2003 | Adams |
| 6,605,098 | B2 | 8/2003 | Nobis et al. |
| 6,626,921 | B2 | 9/2003 | Blatter et al. |
| 6,629,630 | B2 | 10/2003 | Adams |
| 6,631,837 | B1 | 10/2003 | Heck |
| 6,632,227 | B2 | 10/2003 | Adams |
| 6,632,237 | B2 | 10/2003 | Ben-David et al. |
| 6,652,542 | B2 | 11/2003 | Blatter et al. |
| 6,659,327 | B2 | 12/2003 | Heck |
| 6,676,671 | B2 | 1/2004 | Robertson et al. |
| 6,681,979 | B2 | 1/2004 | Whitman |
| 6,685,079 | B2 | 2/2004 | Sharma et al. |
| 6,695,198 | B2 | 2/2004 | Adams et al. |
| 6,695,199 | B2 | 2/2004 | Whitman |
| 6,698,643 | B2 | 3/2004 | Whitman |
| 6,716,222 | B2 | 4/2004 | McAlister et al. |
| 6,716,233 | B1 | 4/2004 | Whitman |
| 6,726,697 | B2 | 4/2004 | Nicholas et al. |
| 6,742,692 | B2 | 6/2004 | Hartwick |
| 6,743,244 | B2 | 6/2004 | Blatter et al. |
| 6,763,993 | B2 | 7/2004 | Bolduc et al. |
| 6,769,590 | B2 | 8/2004 | Vresh et al. |
| 6,769,594 | B2 | 8/2004 | Orban, III |
| 6,820,791 | B2 | 11/2004 | Adams |
| 6,821,282 | B2 | 11/2004 | Perry et al. |
| 6,827,246 | B2 | 12/2004 | Sullivan et al. |
| 6,840,423 | B2 | 1/2005 | Adams et al. |
| 6,843,403 | B2 | 1/2005 | Whitman |
| 6,846,308 | B2 | 1/2005 | Whitman et al. |
| 6,852,122 | B2 | 2/2005 | Rush |
| 6,866,178 | B2 | 3/2005 | Adams et al. |
| 6,872,214 | B2 | 3/2005 | Sonnenschein et al. |
| 6,874,669 | B2 | 4/2005 | Adams et al. |
| 6,884,250 | B2 | 4/2005 | Monassevitch et al. |
| 6,905,504 | B1 | 6/2005 | Vargas |
| 6,938,814 | B2 | 9/2005 | Sharma |
| 6,942,675 | B1 | 9/2005 | Vargas |
| 6,945,444 | B2 | 9/2005 | Gresham et al. |
| 6,953,138 | B1 | 10/2005 | Dworak et al. |
| 6,957,758 | B2 | 10/2005 | Aranyi |
| 6,959,851 | B2 | 11/2005 | Heinrich |
| 6,978,922 | B2 | 12/2005 | Bilotti et al. |
| 6,981,941 | B2 | 1/2006 | Whitman et al. |
| 6,981,979 | B2 | 1/2006 | Nicolo |
| 7,032,798 | B2 | 4/2006 | Whitman et al. |
| 7,059,331 | B2 | 6/2006 | Adams et al. |
| 7,059,510 | B2 | 6/2006 | Orban, III |
| 7,077,856 | B2 | 7/2006 | Whitman |
| 7,080,769 | B2 | 7/2006 | Vresh et al. |
| 7,086,267 | B2 | 8/2006 | Dworak et al. |
| 7,114,642 | B2 | 10/2006 | Whitman |
| 7,118,528 | B1 | 10/2006 | Piskun |
| 7,122,044 | B2 | 10/2006 | Bolduc et al. |
| 7,128,748 | B2 | 10/2006 | Mooradian et al. |
| 7,141,055 | B2 | 11/2006 | Abrams et al. |
| 7,168,604 | B2 | 1/2007 | Milliman et al. |
| 7,179,267 | B2 | 2/2007 | Nolan et al. |
| 7,182,239 | B1 | 2/2007 | Myers |
| 7,195,142 | B2 | 3/2007 | Orban, III |
| 7,207,168 | B2 | 4/2007 | Doepker et al. |
| 7,220,237 | B2 | 5/2007 | Gannoe et al. |
| 7,234,624 | B2 | 6/2007 | Gresham et al. |
| 7,235,089 | B1 | 6/2007 | McGuckin, Jr. |
| RE39,841 | E | 9/2007 | Bilotti et al. |
| 7,285,125 | B2 | 10/2007 | Viola |
| 7,303,106 | B2 | 12/2007 | Milliman et al. |
| 7,303,107 | B2 | 12/2007 | Milliman et al. |
| 7,309,341 | B2 | 12/2007 | Ortiz et al. |
| 7,322,994 | B2 | 1/2008 | Nicholas et al. |
| 7,325,713 | B2 | 2/2008 | Aranyi |
| 7,334,718 | B2 | 2/2008 | McAlister et al. |
| 7,335,212 | B2 | 2/2008 | Edoga et al. |
| 7,364,060 | B2 | 4/2008 | Milliman |
| 7,398,908 | B2 | 7/2008 | Holsten et al. |
| 7,399,305 | B2 | 7/2008 | Csiky et al. |
| 7,401,721 | B2 | 7/2008 | Holsten et al. |
| 7,401,722 | B2 | 7/2008 | Hur |
| 7,407,075 | B2 | 8/2008 | Holsten et al. |
| 7,410,086 | B2 | 8/2008 | Ortiz et al. |
| 7,422,137 | B2 | 9/2008 | Manzo |
| 7,422,138 | B2 | 9/2008 | Bilotti et al. |
| 7,431,191 | B2 | 10/2008 | Milliman |
| 7,438,718 | B2 | 10/2008 | Milliman et al. |
| 7,455,676 | B2 | 11/2008 | Holsten et al. |
| 7,455,682 | B2 | 11/2008 | Viola |
| 7,465,309 | B2 * | 12/2008 | Walen ............... A61B 17/1615 606/167 |
| 7,481,347 | B2 | 1/2009 | Roy |
| 7,494,038 | B2 | 2/2009 | Milliman |
| 7,506,791 | B2 | 3/2009 | Omaits et al. |
| 7,516,877 | B2 | 4/2009 | Aranyi |
| 7,527,185 | B2 | 5/2009 | Harari et al. |
| 7,537,602 | B2 | 5/2009 | Whitman |
| 7,546,939 | B2 | 6/2009 | Adams et al. |
| 7,546,940 | B2 | 6/2009 | Milliman et al. |
| 7,547,312 | B2 | 6/2009 | Bauman et al. |
| 7,556,186 | B2 | 7/2009 | Milliman |
| 7,559,451 | B2 | 7/2009 | Sharma et al. |
| 7,559,927 | B2 * | 7/2009 | Shores ............... A61B 17/162 606/79 |
| 7,585,306 | B2 | 9/2009 | Abbott et al. |
| 7,588,174 | B2 | 9/2009 | Holsten et al. |
| 7,600,663 | B2 | 10/2009 | Green |
| 7,611,038 | B2 | 11/2009 | Racenet et al. |
| 7,635,385 | B2 | 12/2009 | Milliman et al. |
| 7,669,747 | B2 | 3/2010 | Weisenburgh, II et al. |
| 7,686,201 | B2 | 3/2010 | Csiky |
| 7,694,864 | B2 | 4/2010 | Okada et al. |
| 7,699,204 | B2 | 4/2010 | Viola |
| 7,708,181 | B2 | 5/2010 | Cole et al. |
| 7,717,313 | B2 | 5/2010 | Criscuolo et al. |
| 7,721,932 | B2 | 5/2010 | Cole et al. |
| 7,726,539 | B2 | 6/2010 | Holsten et al. |
| 7,743,958 | B2 | 6/2010 | Orban, III |
| 7,744,627 | B2 | 6/2010 | Orban, III et al. |
| 7,770,776 | B2 | 8/2010 | Chen et al. |
| 7,771,440 | B2 | 8/2010 | Ortiz et al. |
| 7,776,060 | B2 | 8/2010 | Mooradian et al. |
| 7,793,813 | B2 | 9/2010 | Bettuchi |
| 7,802,712 | B2 | 9/2010 | Milliman et al. |
| 7,823,592 | B2 | 11/2010 | Bettuchi et al. |
| 7,837,079 | B2 | 11/2010 | Holsten et al. |
| 7,837,080 | B2 | 11/2010 | Schwemberger |
| 7,837,081 | B2 | 11/2010 | Holsten et al. |
| 7,845,536 | B2 | 12/2010 | Viola et al. |
| 7,845,538 | B2 | 12/2010 | Whitman |
| 7,857,187 | B2 | 12/2010 | Milliman |

(56) References Cited

U.S. PATENT DOCUMENTS

| | | |
|---|---|---|
| 7,886,951 B2 | 2/2011 | Hessler |
| 7,896,215 B2 | 3/2011 | Adams et al. |
| 7,900,806 B2 | 3/2011 | Chen et al. |
| 7,909,039 B2 | 3/2011 | Hur |
| 7,909,219 B2 | 3/2011 | Cole et al. |
| 7,909,222 B2 | 3/2011 | Cole et al. |
| 7,909,223 B2 | 3/2011 | Cole et al. |
| 7,913,892 B2 | 3/2011 | Cole et al. |
| 7,918,377 B2 | 4/2011 | Measamer et al. |
| 7,922,062 B2 | 4/2011 | Cole et al. |
| 7,922,743 B2 | 4/2011 | Heinrich et al. |
| 7,931,183 B2 | 4/2011 | Orban, III |
| 7,938,307 B2 | 5/2011 | Bettuchi |
| 7,942,302 B2 | 5/2011 | Roby et al. |
| 7,951,166 B2 | 5/2011 | Orban, III et al. |
| 7,959,050 B2 | 6/2011 | Smith et al. |
| 7,967,181 B2 | 6/2011 | Viola et al. |
| 7,975,895 B2 | 7/2011 | Milliman |
| 8,002,795 B2 | 8/2011 | Beetel |
| 8,006,701 B2 | 8/2011 | Bilotti et al. |
| 8,006,889 B2 | 8/2011 | Adams et al. |
| 8,011,551 B2 | 9/2011 | Marczyk et al. |
| 8,011,554 B2 | 9/2011 | Milliman |
| 8,016,177 B2 | 9/2011 | Bettuchi et al. |
| 8,016,858 B2 | 9/2011 | Whitman |
| 8,020,741 B2 | 9/2011 | Cole et al. |
| 8,025,199 B2 | 9/2011 | Whitman et al. |
| 8,028,885 B2 | 10/2011 | Smith et al. |
| 8,038,046 B2 | 10/2011 | Smith et al. |
| 8,043,207 B2 | 10/2011 | Adams |
| 8,066,167 B2 | 11/2011 | Measamer et al. |
| 8,066,169 B2 | 11/2011 | Viola |
| 8,070,035 B2 | 12/2011 | Holsten et al. |
| 8,070,037 B2 | 12/2011 | Csiky |
| 8,096,458 B2 | 1/2012 | Hessler |
| 8,109,426 B2 | 2/2012 | Milliman et al. |
| 8,109,427 B2 | 2/2012 | Orban, III |
| 8,113,406 B2 | 2/2012 | Holsten et al. |
| 8,113,407 B2 | 2/2012 | Holsten et al. |
| 8,123,103 B2 | 2/2012 | Milliman |
| 8,128,645 B2 | 3/2012 | Sonnenschein et al. |
| 8,132,703 B2 | 3/2012 | Milliman et al. |
| 8,136,712 B2 | 3/2012 | Zingman |
| 8,146,790 B2 | 4/2012 | Milliman |
| 8,146,791 B2 | 4/2012 | Bettuchi et al. |
| 8,181,838 B2 | 5/2012 | Milliman et al. |
| 8,192,460 B2 | 6/2012 | Orban, III et al. |
| 8,201,720 B2 | 6/2012 | Hessler |
| 8,203,782 B2 | 6/2012 | Brueck et al. |
| 8,211,130 B2 | 7/2012 | Viola |
| 8,225,799 B2 | 7/2012 | Bettuchi |
| 8,225,981 B2 | 7/2012 | Criscuolo et al. |
| 8,231,041 B2 | 7/2012 | Marczyk et al. |
| 8,231,042 B2 | 7/2012 | Hessler et al. |
| 8,257,391 B2 | 9/2012 | Orban, III et al. |
| 8,267,301 B2 | 9/2012 | Milliman et al. |
| 8,272,552 B2 | 9/2012 | Holsten et al. |
| 8,276,802 B2 | 10/2012 | Kostrzewski |
| 8,281,975 B2 | 10/2012 | Criscuolo et al. |
| 8,286,845 B2 | 10/2012 | Perry et al. |
| 8,308,045 B2 | 11/2012 | Bettuchi et al. |
| 8,312,885 B2 | 11/2012 | Bettuchi et al. |
| 8,313,014 B2 | 11/2012 | Bettuchi |
| 8,317,073 B2 | 11/2012 | Milliman et al. |
| 8,317,074 B2 | 11/2012 | Ortiz et al. |
| 8,322,590 B2 | 12/2012 | Patel et al. |
| 8,328,060 B2 | 12/2012 | Jankowski et al. |
| 8,328,062 B2 | 12/2012 | Viola |
| 8,328,063 B2 | 12/2012 | Milliman et al. |
| 8,343,185 B2 | 1/2013 | Milliman et al. |
| 8,353,438 B2 | 1/2013 | Baxter, III et al. |
| 8,353,439 B2 | 1/2013 | Baxter, III et al. |
| 8,353,930 B2 | 1/2013 | Heinrich et al. |
| 8,360,295 B2 | 1/2013 | Milliman et al. |
| 8,365,974 B2 | 2/2013 | Milliman |
| 8,403,942 B2 | 3/2013 | Milliman et al. |
| 8,408,441 B2 | 4/2013 | Wenchell et al. |
| 8,413,870 B2 | 4/2013 | Pastorelli et al. |
| 8,413,872 B2 | 4/2013 | Patel |
| 8,418,905 B2 | 4/2013 | Milliman |
| 8,418,909 B2 | 4/2013 | Kostrzewski |
| 8,424,535 B2 | 4/2013 | Hessler et al. |
| 8,424,741 B2 | 4/2013 | McGuckin, Jr. et al. |
| 8,430,291 B2 | 4/2013 | Heinrich et al. |
| 8,430,292 B2 | 4/2013 | Patel et al. |
| 8,453,910 B2 | 6/2013 | Bettuchi et al. |
| 8,453,911 B2 | 6/2013 | Milliman et al. |
| 8,485,414 B2 | 7/2013 | Criscuolo et al. |
| 8,490,853 B2 | 7/2013 | Criscuolo et al. |
| 8,511,533 B2 | 8/2013 | Viola et al. |
| 8,551,138 B2 | 10/2013 | Orban, III et al. |
| 8,567,655 B2 | 10/2013 | Nalagatla et al. |
| 8,579,178 B2 | 11/2013 | Holsten et al. |
| 8,590,763 B2 | 11/2013 | Milliman |
| 8,590,764 B2 | 11/2013 | Hartwick et al. |
| 8,608,047 B2 | 12/2013 | Holsten et al. |
| 8,616,428 B2 | 12/2013 | Milliman et al. |
| 8,616,429 B2 | 12/2013 | Viola |
| 8,622,275 B2 | 1/2014 | Baxter, III et al. |
| 8,631,993 B2 | 1/2014 | Kostrzewski |
| 8,636,187 B2 | 1/2014 | Hueil et al. |
| 8,640,940 B2 | 2/2014 | Ohdaira |
| 8,662,370 B2 | 3/2014 | Takei |
| 8,663,258 B2 | 3/2014 | Bettuchi et al. |
| 8,672,931 B2 | 3/2014 | Goldboss et al. |
| 8,678,264 B2 | 3/2014 | Racenet et al. |
| 8,684,248 B2 | 4/2014 | Milliman |
| 8,684,250 B2 | 4/2014 | Bettuchi et al. |
| 8,684,251 B2 | 4/2014 | Rebuffat et al. |
| 8,684,252 B2 | 4/2014 | Patel et al. |
| 8,733,611 B2 | 5/2014 | Willman |
| 8,801,713 B2 * | 8/2014 | del Rio ............ A61B 17/1615 606/80 |
| 9,414,848 B2 * | 8/2016 | Edwards ............ A61B 17/1633 |
| 9,504,478 B2 * | 11/2016 | Edwards ............ A61B 17/162 |
| 9,877,763 B2 * | 1/2018 | Barth .................. A61B 17/162 |
| 9,974,540 B2 * | 5/2018 | Richard ........... A61B 17/07207 |
| 2003/0023256 A1 * | 1/2003 | Estes ................. A61B 17/1633 606/167 |
| 2003/0111507 A1 | 6/2003 | Nunez |
| 2004/0059227 A1 | 3/2004 | Nita et al. |
| 2004/0194324 A1 | 10/2004 | Youn-Chyuan |
| 2005/0051597 A1 | 3/2005 | Toledano |
| 2005/0107813 A1 | 5/2005 | Gilete Garcia |
| 2006/0000869 A1 | 1/2006 | Fontayne |
| 2006/0011698 A1 | 1/2006 | Okada et al. |
| 2006/0201989 A1 | 9/2006 | Ojeda |
| 2007/0027473 A1 | 2/2007 | Vresh et al. |
| 2007/0029363 A1 | 2/2007 | Popov |
| 2007/0060952 A1 | 3/2007 | Roby et al. |
| 2007/0083208 A1 * | 4/2007 | Desarzens .......... A61B 17/1666 606/80 |
| 2008/0058801 A1 * | 3/2008 | Taylor ................. A61B 18/042 606/45 |
| 2008/0179375 A1 | 7/2008 | Scirica |
| 2008/0308605 A1 | 12/2008 | Scirica |
| 2009/0236392 A1 | 9/2009 | Cole et al. |
| 2009/0236398 A1 | 9/2009 | Cole et al. |
| 2009/0236401 A1 | 9/2009 | Cole et al. |
| 2009/0326540 A1 | 12/2009 | Estes |
| 2010/0019016 A1 | 1/2010 | Edoga et al. |
| 2010/0051668 A1 | 3/2010 | Milliman et al. |
| 2010/0084453 A1 | 4/2010 | Hu |
| 2010/0147923 A1 | 6/2010 | D'Agostino et al. |
| 2010/0163598 A1 | 7/2010 | Belzer |
| 2010/0224668 A1 | 9/2010 | Fontayne et al. |
| 2010/0230465 A1 | 9/2010 | Smith et al. |
| 2010/0258611 A1 | 10/2010 | Smith et al. |
| 2010/0264195 A1 | 10/2010 | Bettuchi |
| 2010/0327041 A1 | 12/2010 | Milliman et al. |
| 2011/0011916 A1 | 1/2011 | Levine |
| 2011/0114697 A1 | 5/2011 | Baxter, III et al. |
| 2011/0114700 A1 | 5/2011 | Baxter, III et al. |
| 2011/0144640 A1 | 6/2011 | Heinrich et al. |

(56) References Cited

U.S. PATENT DOCUMENTS

| | | |
|---|---|---|
| 2011/0147432 A1 | 6/2011 | Heinrich et al. |
| 2011/0186614 A1 | 8/2011 | Kasvikis |
| 2011/0192882 A1 | 8/2011 | Hess et al. |
| 2011/0276036 A1 | 11/2011 | Spranger et al. |
| 2012/0061448 A1 | 3/2012 | Zingman |
| 2012/0145755 A1 | 6/2012 | Kahn |
| 2012/0193395 A1 | 8/2012 | Pastorelli et al. |
| 2012/0193398 A1 | 8/2012 | Williams et al. |
| 2012/0232339 A1 | 9/2012 | Csiky |
| 2012/0273548 A1 | 11/2012 | Ma et al. |
| 2012/0325888 A1 | 12/2012 | Qiao et al. |
| 2013/0015232 A1 | 1/2013 | Smith et al. |
| 2013/0020372 A1 | 1/2013 | Jankowski et al. |
| 2013/0020373 A1 | 1/2013 | Smith et al. |
| 2013/0032628 A1 | 2/2013 | Li et al. |
| 2013/0056516 A1 | 3/2013 | Viola |
| 2013/0060258 A1 | 3/2013 | Giacomantonio |
| 2013/0093149 A1* | 4/2013 | Saur .................. B25B 21/00 279/143 |
| 2013/0096591 A1 | 4/2013 | Hart et al. |
| 2013/0105544 A1 | 5/2013 | Mozdzierz et al. |
| 2013/0105546 A1 | 5/2013 | Milliman et al. |
| 2013/0105551 A1 | 5/2013 | Zingman |
| 2013/0123705 A1 | 5/2013 | Holm et al. |
| 2013/0126580 A1 | 5/2013 | Smith et al. |
| 2013/0138129 A1* | 5/2013 | Garrison .............. A61B 17/285 606/170 |
| 2013/0153630 A1 | 6/2013 | Miller et al. |
| 2013/0153631 A1 | 6/2013 | Vasudevan et al. |
| 2013/0153633 A1 | 6/2013 | Casasanta, Jr. et al. |
| 2013/0153634 A1 | 6/2013 | Carter et al. |
| 2013/0153638 A1 | 6/2013 | Carter et al. |
| 2013/0153639 A1 | 6/2013 | Hodgkinson et al. |
| 2013/0175315 A1 | 7/2013 | Milliman |
| 2013/0175318 A1 | 7/2013 | Felder et al. |
| 2013/0175319 A1 | 7/2013 | Felder et al. |
| 2013/0175320 A1 | 7/2013 | Mandakolathur Vasudevan et al. |
| 2013/0181029 A1 | 7/2013 | Milliman |
| 2013/0181035 A1 | 7/2013 | Milliman |
| 2013/0181036 A1 | 7/2013 | Olson et al. |
| 2013/0186930 A1 | 7/2013 | Wenchell et al. |
| 2013/0193185 A1 | 8/2013 | Patel |
| 2013/0193187 A1 | 8/2013 | Milliman |
| 2013/0193190 A1 | 8/2013 | Carter et al. |
| 2013/0193191 A1 | 8/2013 | Stevenson et al. |
| 2013/0193192 A1 | 8/2013 | Casasanta, Jr. et al. |
| 2013/0200131 A1 | 8/2013 | Racenet et al. |
| 2013/0206816 A1 | 8/2013 | Penna |
| 2013/0214027 A1 | 8/2013 | Hessler et al. |
| 2013/0214028 A1 | 8/2013 | Patel et al. |
| 2013/0228609 A1 | 9/2013 | Kostrzewski |
| 2013/0240597 A1 | 9/2013 | Milliman et al. |
| 2013/0240600 A1 | 9/2013 | Bettuchi |
| 2013/0248581 A1 | 9/2013 | Smith et al. |
| 2013/0277411 A1 | 10/2013 | Hodgkinson et al. |
| 2013/0277412 A1 | 10/2013 | Gresham et al. |
| 2013/0284792 A1 | 10/2013 | Ma |
| 2013/0292449 A1 | 11/2013 | Bettuchi et al. |
| 2013/0299553 A1 | 11/2013 | Mozdzierz |
| 2013/0299554 A1 | 11/2013 | Mozdzierz |
| 2013/0306701 A1 | 11/2013 | Olson |
| 2013/0306707 A1 | 11/2013 | Viola et al. |
| 2014/0008413 A1 | 1/2014 | Williams |
| 2014/0012317 A1 | 1/2014 | Orban et al. |
| 2014/0243868 A1* | 8/2014 | Parihar .................. A61B 17/29 606/185 |
| 2014/0249474 A1* | 9/2014 | Suon .................. A61B 17/2909 604/95.04 |
| 2014/0309677 A1 | 10/2014 | Baldwin |
| 2015/0108201 A1 | 4/2015 | Williams |
| 2015/0320420 A1* | 11/2015 | Penna .................. A61B 17/1155 227/176.1 |
| 2016/0157856 A1* | 6/2016 | Williams .............. A61B 17/068 227/175.1 |
| 2016/0182934 A1 | 6/2016 | Nichols et al. |
| 2016/0192938 A1* | 7/2016 | Sgroi, Jr. ............ A61B 17/1155 227/175.1 |
| 2016/0192939 A1* | 7/2016 | Sgroi, Jr. ............ A61B 17/1155 227/176.1 |
| 2017/0079660 A1* | 3/2017 | Sgroi .................. A61B 17/068 |
| 2018/0008272 A1* | 1/2018 | Sgroi, Jr. ............ A61B 17/072 |
| 2018/0125495 A1* | 5/2018 | Sgroi, Jr. ............ A61B 17/1155 |

FOREIGN PATENT DOCUMENTS

| | | |
|---|---|---|
| DE | 1057729 B | 5/1959 |
| DE | 3301713 A1 | 7/1984 |
| EP | 0152382 A2 | 8/1985 |
| EP | 0173451 A1 | 3/1986 |
| EP | 0190022 A2 | 8/1986 |
| EP | 0282157 A1 | 9/1988 |
| EP | 0503689 A2 | 9/1992 |
| EP | 1190796 A1 | 3/2002 |
| EP | 1354560 A2 | 10/2003 |
| EP | 1631199 A1 | 3/2006 |
| EP | 2090245 A1 | 8/2009 |
| EP | 2524656 A2 | 11/2012 |
| EP | 2774549 A2 | 9/2014 |
| EP | 3031407 A1 | 6/2016 |
| EP | 3042619 A1 | 7/2016 |
| FR | 1136020 A | 5/1957 |
| FR | 1461464 A | 2/1966 |
| FR | 1588250 A | 4/1970 |
| FR | 2243758 A1 | 4/1975 |
| FR | 2443239 A1 | 7/1980 |
| GB | 1185292 A | 3/1970 |
| GB | 2016991 A | 9/1979 |
| GB | 2070499 A | 9/1981 |
| JP | H08233182 A | 9/1996 |
| JP | H1163347 A | 3/1999 |
| NL | 7711347 A | 4/1979 |
| SU | 1509052 A1 | 9/1989 |
| WO | 8706448 A1 | 11/1987 |
| WO | 8900406 A1 | 1/1989 |
| WO | 9006085 A1 | 6/1990 |
| WO | 9805261 A2 | 2/1998 |
| WO | 2001/054594 A1 | 8/2001 |
| WO | 2004107990 A1 | 12/2004 |
| WO | 2008/107918 A1 | 9/2008 |
| WO | 2012015917 A1 | 2/2012 |
| WO | 2014139327 A1 | 9/2014 |
| WO | 2014139440 A1 | 9/2014 |
| WO | 2014139442 A1 | 9/2014 |
| WO | 2014139467 A1 | 9/2014 |
| WO | 20140139442 A1 | 9/2014 |

OTHER PUBLICATIONS

Partial European Search Report dated Jan. 16, 2017, issued in EP Appln. No. 16180339.

European Search Report dated Nov. 30, 2016, issued in EP Application No. 16181395.

EP Examination Report dated Jun. 20, 2017, issued in EP Application No. 16150288.

European Search Report dated Dec. 7, 2017, issued in EP Application No. 17180237.

U.S. Appl. No. 62/100,512, filed Jan. 7, 2015, inventor: Williams et al.

U.S. Appl. No. 62/150,913, filed Apr. 22, 2015, inventor: Penna et al.

U.S. Appl. No. 14/591,193, filed Jan. 7, 2015, inventor: Sgroi, Jr.

U.S. Appl. No. 14/810,811, filed Jul. 28, 2015, inventor: Sgroi, Jr., et al.

U.S. Appl. No. 14/805,547, filed Jul. 22, 2015, inventor: Scirica, et al.

U.S. Appl. No. 14/859,590, filed Sep. 21, 2015, inventor: Sgroi.

U.S. Appl. No. 14/804,814, filed Jul. 21, 2015, inventor: Williams et al.

European Search Report dated May 10, 2016, issued in EP Application No. 15198203.

(56) References Cited

OTHER PUBLICATIONS

European Search Report dated May 17, 2016, issued in EP Application No. 16150284.
European Search Report dated Jun. 24, 2016, issued in EP Application No. 16150288.5.
European Search Report dated May 23, 2017, issued in EP Application No. 16189648.
Australian Examination Report dated May 26, 2021, issued in corresponding Australian Appln. No. 2017204220, 5 pages.

* cited by examiner

LOADING UNIT LOCKING COLLAR WITH LINEARLY ACTUATED RELEASE

BACKGROUND

1. Technical Field

The present disclosure relates generally to surgical stapling instruments. More specifically, the present disclosure relates to circular surgical stapling instruments including replaceable loading units.

2. Background of Related Art

Surgical stapling instruments configured to join tissue portions during a surgical procedure are well known. These instruments include linear end effectors which are oriented parallel or transverse to a longitudinal axis of the instrument as well as circular end effectors. Typically, linear stapling instruments include a disposable loading unit or a replaceable cartridge that allows the stapling instrument to be used multiple times. However, conventional circular stapling instruments include a cartridge or shell assembly that is typically fixedly attached to the instrument such that the instrument must be disposed of after a single use. Some circular stapling instruments include a cartridge or shell assembly that is replaceable.

A need exists in the art for a simple, inexpensive instrument for releasably securing a cartridge or shell assembly to a circular stapling instrument to facilitate reuse of the stapling instrument.

SUMMARY

In an aspect of the present disclosure, a loading unit includes a shell assembly, a lock collar, and a release collar. The shell assembly has a coupling ring that defines a lock slot and a proximal opening configured to receive a distal end portion of a surgical instrument. The lock collar is disposed about the coupling ring and has a radially extending lock that is configured to be received within the lock slot. The lock collar is transitionable between a locked configuration in which the lock is positioned within the lock slot and an unlocked configuration in which the lock is lifted from within the lock slot. The lock collar is configured to secure the loading unit to a surgical instrument in the locked configuration. The release collar is disposed about the coupling ring proximal of the lock collar and is transitionable between an unactuated position and an actuated position. The release collar transitioning the lock collar to the unlocked configuration as the release collar is translated from the unactuated position towards the actuated position.

In some aspects, the locking collar includes a lock ring and a first resilient locking flange extending proximally from the lock ring. The first locking flange may support the lock which passes through the lock slot and into the proximal opening in the locked configuration and is positioned outside of the proximal opening in the unlocked configuration. The first locking flange may include a cam surface that is angled distally inward and the release collar may have a first camming surface that is angled proximally outward. In the locked configuration, the cam surface of the first locking collar may engage the first camming surface of the release collar to urge the release collar towards the unactuated position. In the actuated position, the first camming surface may engage the cam surface of the first locking flange to transition the lock collar to the unlocked configuration.

In certain aspects, the lock collar urges the release collar towards the unactuated position. The lock collar may include a second resilient locking flange that extends proximally from the lock ring and that opposes the first locking flange. The second locking flange may have a cam surface that is angled distally inward and the release collar may have a second camming surface that is angled proximally outward. The cam surface of the second locking flange may engage the second camming surface of the release collar to urge the release collar towards the unactuated position. In the actuated position of the release collar, the second camming surface may lift the second locking flange away from the coupling ring.

In particular aspects, the coupling ring may defines a plurality of lock collar retention slots and the lock collar includes a plurality of lock collar retention tabs that are each received within a respective lock collar retention slot to secure the lock collar to the coupling ring. The coupling ring may define a plurality of release collar retention slots and the release collar may include a plurality of release collar retention tabs which are each slidably received within a respective release collar retention slot to retain the release collar about the coupling ring.

In another aspect of the present disclosure, a surgical system includes a surgical instrument, a loading unit, a lock collar, and a release collar. The surgical instrument includes a distal end portion that defines a locking window. The loading unit includes a shell assembly that has a coupling ring which defines a proximal opening that receives the distal end portion. The coupling ring defines a lock slot. The lock collar is disposed about the coupling ring and includes a radially extending lock that is configured to be received within the lock slot. The lock collar is transitionable between a locked configuration in which the lock is positioned within the lock slot and an unlocked configuration in which the lock is lifted from within the lock slot. The lock collar is configured to secure the loading unit to the distal end portion of the surgical instrument in the locked configuration. The release collar is disposed about the coupling ring that is proximal of the lock collar. The release collar is translatable between an unactuated position and an actuated position. The release collar transitions the lock collar to the unlocked configuration as the release collar is translated from the unactuated position towards the actuated position.

In aspects, the coupling ring includes a key that extends into the proximal opening and the distal end portion of the surgical instrument defines a keyway. The key may be parallel to a longitudinal axis of the shell assembly and the keyway may be parallel to a longitudinal axis of the distal end portion of the surgical instrument. The key may be received within the keyway to rotatably fix the loading unit to the distal end portion of the surgical instrument.

In some aspects, the lock collar may include a lock ring and a first resilient locking flange that extends proximally from the lock ring. The first locking flange may support the lock which includes a cam surface angled distally inward. A distal end of the surgical instrument may be configured to engage the cam surface of the lock to transition the lock collar to the unlocked configuration as the distal end portion of the surgical instrument is received within the proximal opening until the locking window is aligned with the lock slot of the coupling ring. The release collar may include alignment indicia and the distal end portion of the surgical instrument may include an alignment indicator. When the distal end portion is received within the proximal opening, the alignment indicial of the release collar and the alignment indicator of the distal end portion may be aligned with one another to align a lock of the lock ring with the locking window of the distal end portion.

In another aspect of the present disclosure, a method of securing a loading unit to a surgical instrument includes aligning a coupling ring of the loading unit with a distal end portion of the surgical instrument, sliding the coupling ring over the distal end portion of the surgical instrument, and continuing to slide the loading unit over the distal end portion until a locking window that is defined in the distal end portion of the surgical instrument is aligned with a lock. Sliding the coupling ring over the distal end portion may include a distal end of the surgical instrument engaging the lock, which is disposed on a lock collar that is disposed over the coupling ring, to lift the lock. The lock is supported on a first locking flange of the locking collar. The lock collar also includes a second locking flange that opposes the first locking flange. The second locking flange engages a release collar that is disposed about the coupling ring proximal of the lock ring to urge the release collar proximally. When the lock is aligned with the locking window, resilience of the locking flange moves the lock into the locking window to secure the loading unit to the surgical instrument.

In aspects, the method includes releasing the loading unit from the distal end portion of the surgical instrument by actuating the release collar distally along the coupling ring to lift the lock from within the locking window and sliding the loading unit off of the distal end portion of the surgical instrument. Actuating the release collar distally may include engaging a cam surface of the first locking flange with a first camming surface of the release collar to lift the lock from within the locking window.

In some aspects, the method includes releasing the release collar after sliding the loading unit off of the distal end portion of the surgical instrument such that the first cam surface engages the first camming surface to urge the release collar proximally along the coupling ring in response to resilience of the first locking flange.

In certain aspects, actuating the release collar distally includes engaging a cam surface of the second locking flange with a second camming surface of the release collar to lift the second locking flange. Aligning the coupling ring of the loading unit with the distal end portion of the surgical instrument includes aligning alignment indicia of the release collar with an alignment indicator of the distal end portion.

Further, to the extent consistent, any of the aspects described herein may be used in conjunction with any or all of the other aspects described herein.

BRIEF DESCRIPTION OF THE DRAWINGS

Various aspects of the present disclosure are described hereinbelow with reference to the drawings, which are incorporated in and constitute a part of this specification, wherein.

DETAILED DESCRIPTION OF EMBODIMENTS

Figure 1:
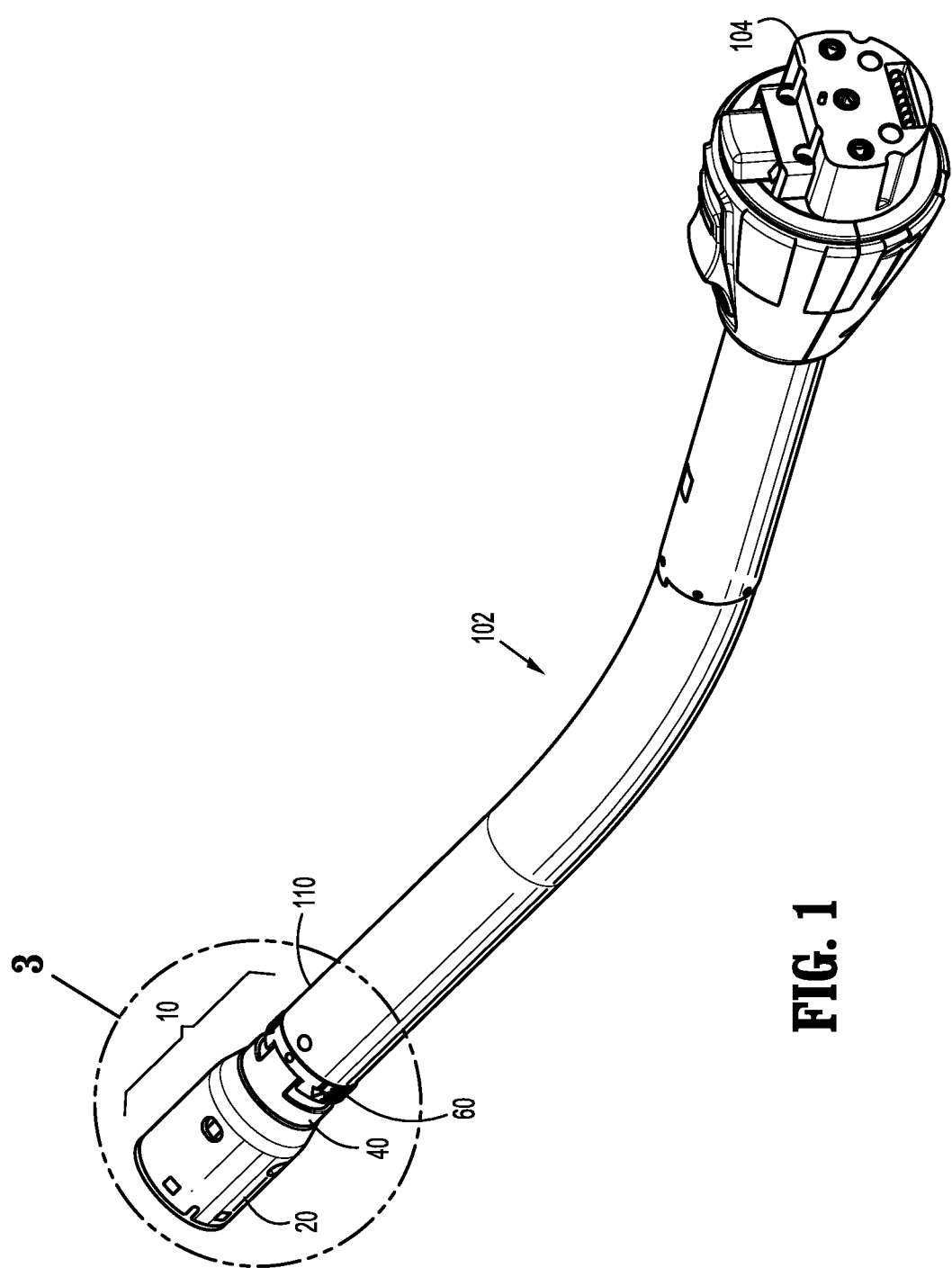
FIG. 1 is a perspective view of a circular stapling adapter with a loading unit releasably coupled to a distal end of the circular stapling adapter in accordance with the present disclosure.

Embodiments of the present disclosure are now described in detail with reference to the drawings in which like reference numerals designate identical or corresponding elements in each of the several views. As used herein, the term "clinician" refers to a doctor, a nurse, or any other care provider and may include support personnel. Throughout this description, the term "proximal" refers to the portion of the device or component thereof that is closest to the clinician and the term "distal" refers to the portion of the device or component thereof that is farthest from the clinician.

This disclosure relates generally to a loading unit including a coupling ring that supports a lock collar and a release collar. The release collar is actuatable to transition the lock collar from a locked configuration where the lock collar secures the loading unit to a surgical instrument to an unlocked configuration where the loading unit is removable from a surgical instrument.

Figure 2:
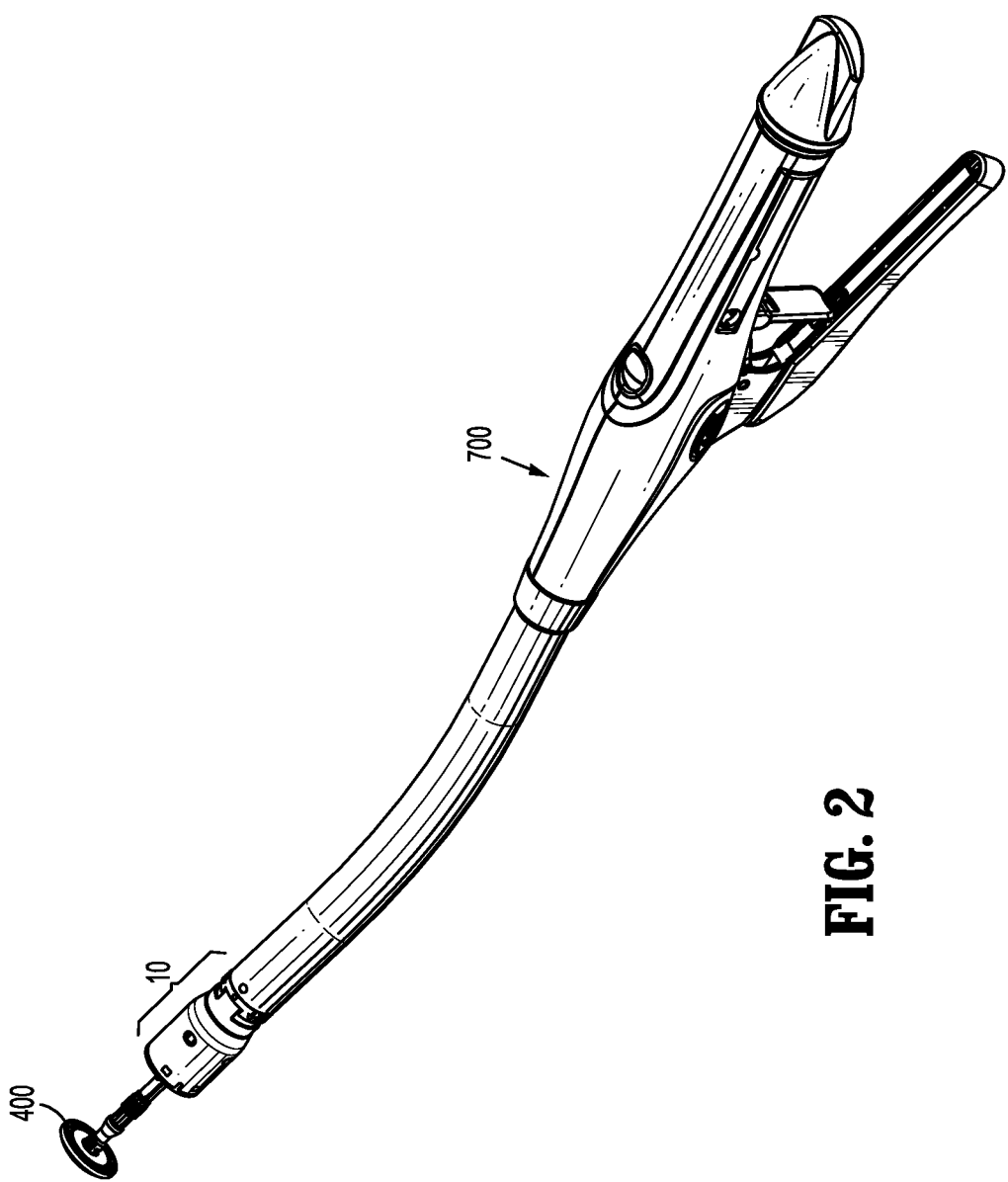
FIG. 2 is a perspective view of a circular stapling surgical instrument with the loading unit of FIG. 1 releasably coupled to a distal end of the surgical instrument.
Figure 3:
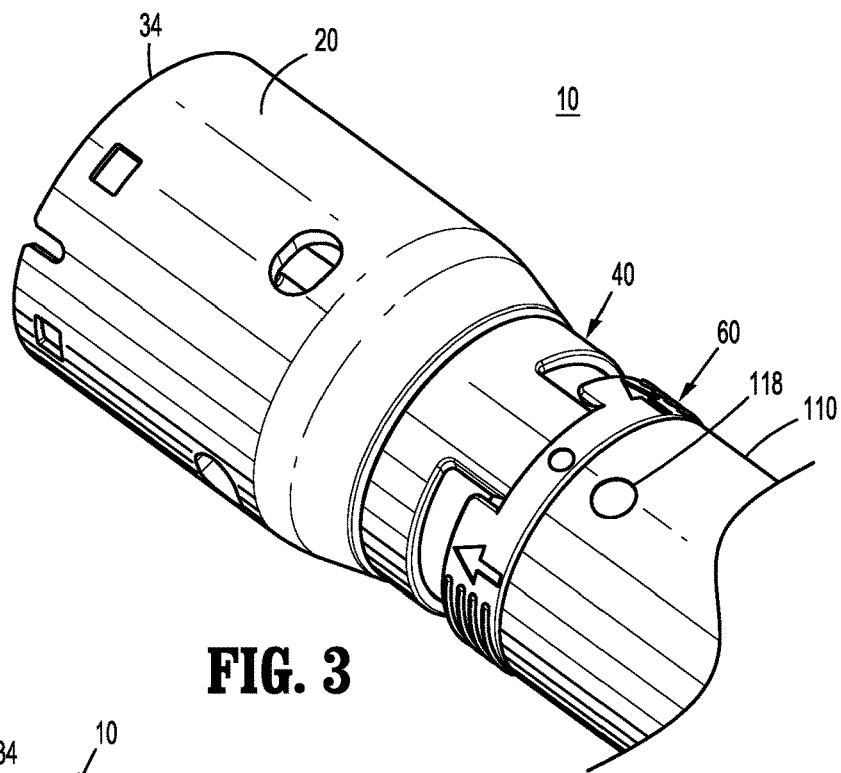
FIG. 3 is an enlarged perspective view of the indicated area of detail of FIG. 1.

With reference to FIGS. 1-3, a loading unit 10 is provided in accordance with embodiments of the present disclosure. The loading unit 10 is configured for selective connection to a powered hand held electromechanical instrument (not shown) via an adapter 102 of the surgical instrument. Alternatively, the loading unit 10 can be configured for connection directly to a manually actuated handle assembly or stapling instrument 700 (FIG. 2) such as described in U.S. Pat. No. 8,789,737 ("the '737 Patent"), which is incorporated herein by reference. In the illustrated embodiment, the loading unit 10 is releasably coupled to a distal end portion 110 of the adapter 102 and includes a staple cartridge 12 (FIG. 5), a shell assembly 20, a lock collar 40, and a release collar 60. The adapter 102 supports an anvil 400 (FIG. 2). The adapter 102 is configured to translate movement of an actuator of the stapling instrument, e.g., an electromechanical actuator (not shown), to move the anvil assembly 400 in relation to the shell assembly 200 and to actuate the shell assembly 20 to suture and cut tissue (not shown). A proximal end 104 of the adapter 102 is attachable to the stapling instrument to actuate the staple cartridge 12. It is contemplated that the proximal end 104 of the adapter 102 may be attached to a manually actuated instrument such as described in the '737 Patent to actuate the staple cartridge 12.

For a detailed description of the structure and function of an exemplary adapter and loading unit, please refer to commonly owned U.S. patent application Ser. No. 14/875,766, filed Oct. 6, 2015. For a detailed description of the structure and function of an exemplary electromechanical instrument, please refer to commonly owned U.S. Pat. Nos. 8,968,276 and 9,055,943, commonly owned U.S. Patent Publication No. 2015/0157321, and commonly owned U.S. Provisional Patent Application Ser. No. 62/291,775, filed Feb. 5, 2016, entitled "HANDHELD ELECTROMECHANICAL SURGICAL SYSTEM." The entire contents of each of these disclosures is incorporated herein by reference.

Figure 4:
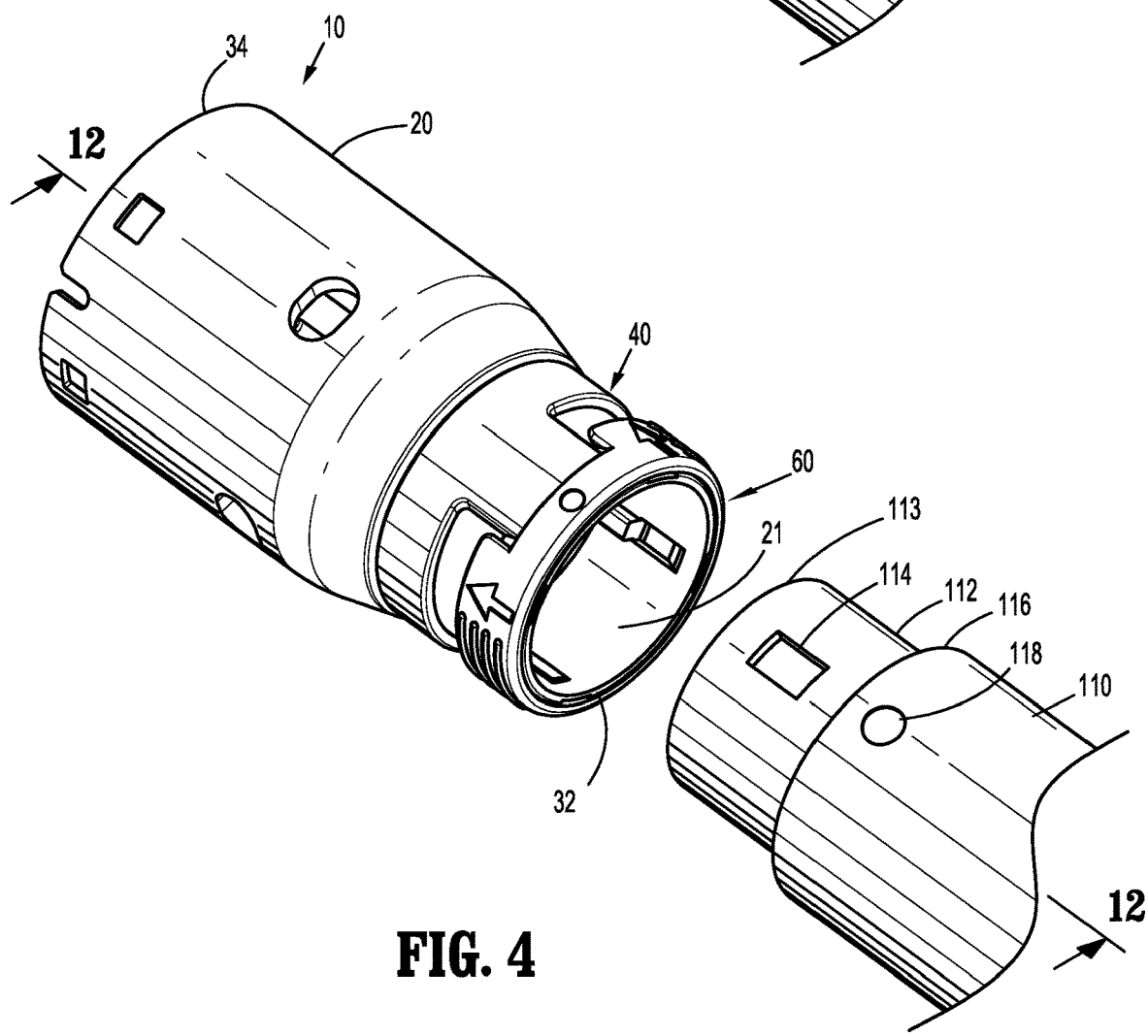
FIG. 4 is a perspective view of the adapter of FIG. 1 with the loading unit decoupled from the adapter.

Referring to FIGS. 3 and 4, the distal end portion 110 of surgical instrument, e.g., the adapter 102, includes a recessed mounting ring 112 that defines a locking window 114. The mounting ring 112 has a reduced diameter to form a shoulder 116 in the distal end portion 110. The shoulder 116 acts as a stop for the loading unit 10 as detailed below. The locking window 114 passes through the outer surface of the mounting ring 112 and is spaced-apart from a distal end 113 of the mounting ring 112. The distal end portion 110 may also define a keyway 119 (FIG. 6) that extends from the distal end 113 of the mounting ring 112 parallel to a longitudinal axis of the adapter 102.

Figure 5:
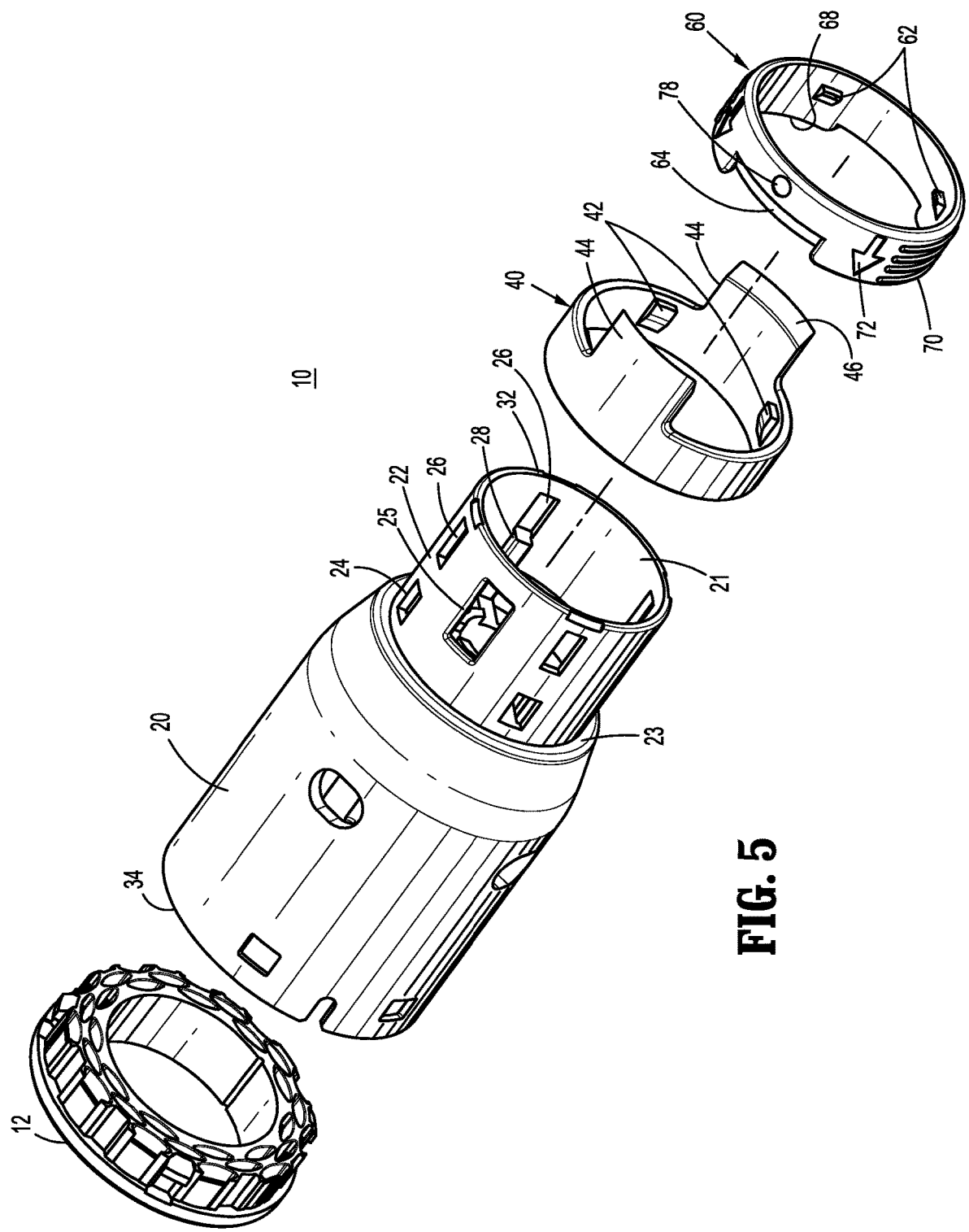
FIG. 5 is an exploded view with parts separated of the loading unit of FIG. 4.
Figure 12:
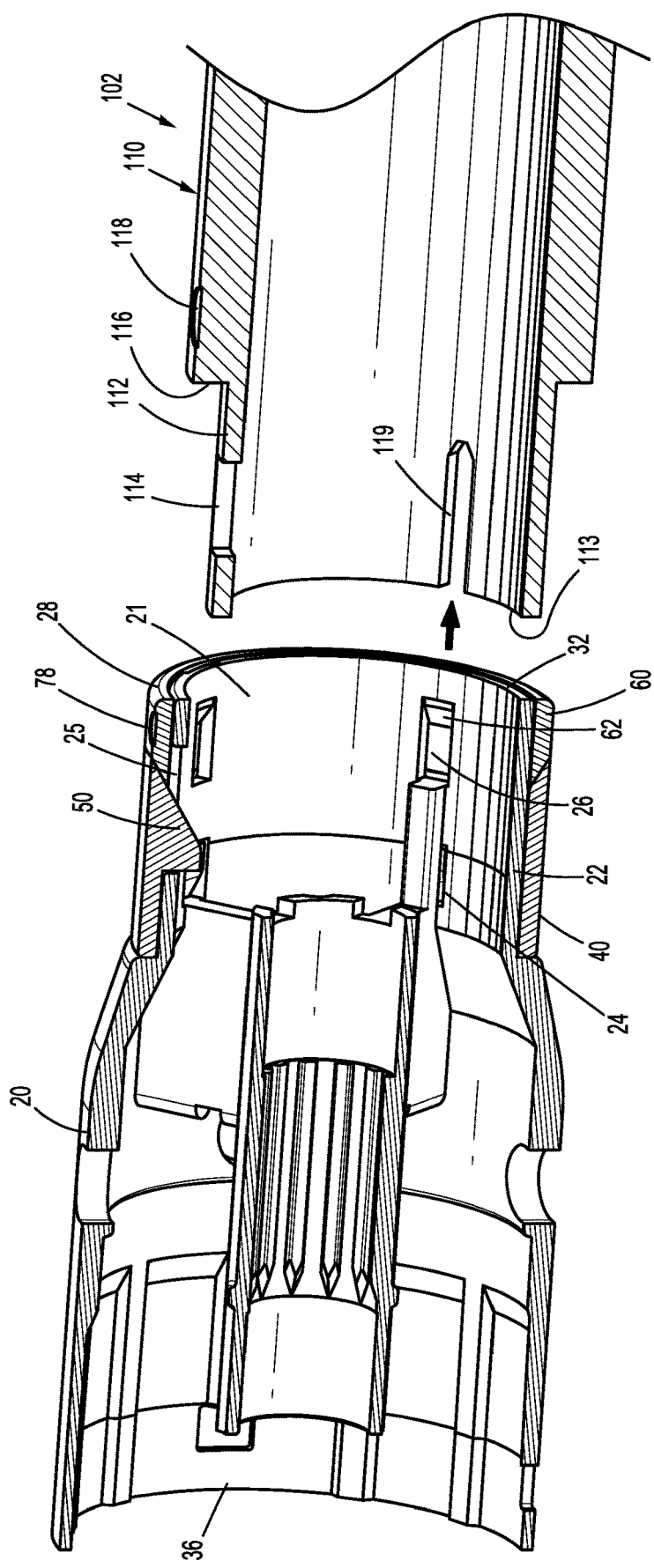
FIG. 12 is a cross-sectional view of taken along section line 12-12 of FIG. 4 illustrating the lock collar in a locked configuration and the release collar in an unactuated position.

Referring also to FIG. 5, the loading unit 10 includes a shell assembly 20, a lock collar 40, and a release collar 60. The shell assembly 20 has a proximal end 32 that includes a recessed coupling ring 22 that defines a cylindrical opening 21 dimensioned to receive the mounting ring 112 of the adapter 102 and a distal end 34 that defines a receptacle 36 (FIG. 12) dimensioned to receive the staple cartridge 12.

With particular reference to FIG. 5, the coupling ring 22 of the shell assembly 20 is sized to be received through the lock collar 40 and the release collar 60 with the release collar 60 positioned proximal of the lock collar 40. In embodiments, the lock collar 40 has a thickness substantially equal to the depth of a step 23 defined by the coupling ring 22 such that the lock collar 40 and the outer surface of the shell assembly 20 form a continuous or smooth surface.

The coupling ring 22 defines lock collar retention slots 24, a lock slot 25, and release collar retention slots 26 that pass through the coupling ring 22 of the shell assembly 20. The lock collar retention slots 24 are configured to receive a portion of the lock collar 40 to longitudinally and radially secure the lock collar 40 in relation to the coupling ring 22 of the shell assembly 20. In embodiments, the lock collar retention slots 24 are substantially rectangular in shape and are disposed about the coupling ring 22. The lock collar retention slots 24 are spaced an equal distance from the step 23 of the shell assembly 20 and are uniformly spaced about the coupling ring 22 (e.g., at 90° apart); however, it is contemplated that the lock collar retention slots 24 may assume a variety of configurations and/or be non-uniformly spaced about the coupling ring 22 to properly orient the lock collar 40 in relation to the coupling ring 22. It is envisioned that the coupling ring 22 can define greater than or less than four lock collar retention slots 24. Each of the lock collar retention slots 24 passes through the outer surface of the coupling ring 22 and may pass through inner and outer surfaces of the coupling ring 22.

The release collar retention slots 26 are configured to receive a portion of the release collar 60 to axially secure the release collar 60 in relation to the coupling ring 22 of the shell assembly 20. As shown, the release collar retention slots 26 are substantially rectangular in shape and are disposed about the coupling ring 22. The release collar retention slots 26 are spaced an equal distance from the proximal end 32 of the shell assembly 20 and are uniformly spaced about the coupling ring 22 (e.g., at 90° apart); however, it is contemplated that the release collar retention slots 26 may assume a variety of configurations and/or be non-uniformly spaced about the coupling ring 22 to orient the release collar 60 in relation to the coupling ring 22. It is envisioned that the coupling ring 22 can define greater than or less than four release collar retention slots 26. As shown, the release collar retention slots 26 are aligned with a respective one of the lock collar retention slots 24; however, it is envisioned that the release collar retention slots 26 can be misaligned from the lock collar retention slots 24. The release collar retention slots 26 pass through the outer surface of the coupling ring 22 and may pass through inner and outer surfaces of the coupling ring 22.

The lock slot 25 passes through inner and outer surfaces of the coupling ring 22 and is configured to receive a portion of the lock collar 40 to secure the shell assembly 20 to the distal end portion 110 of the adapter 102 as described in detail below. The lock slot 25 has a substantially rectangular shape and passes between an outer surface and an inner surface of the coupling ring 22. The lock slot 25 may be oriented such that the walls defining the lock slot 25 are parallel and perpendicular to the longitudinal axis of the shell assembly 20. The lock slot 25 is positioned between two of the lock collar retention slots 24. It is envisioned that the lock slot 25 may be in communication with one or more of the release collar retention slots 26.

Figure 6:
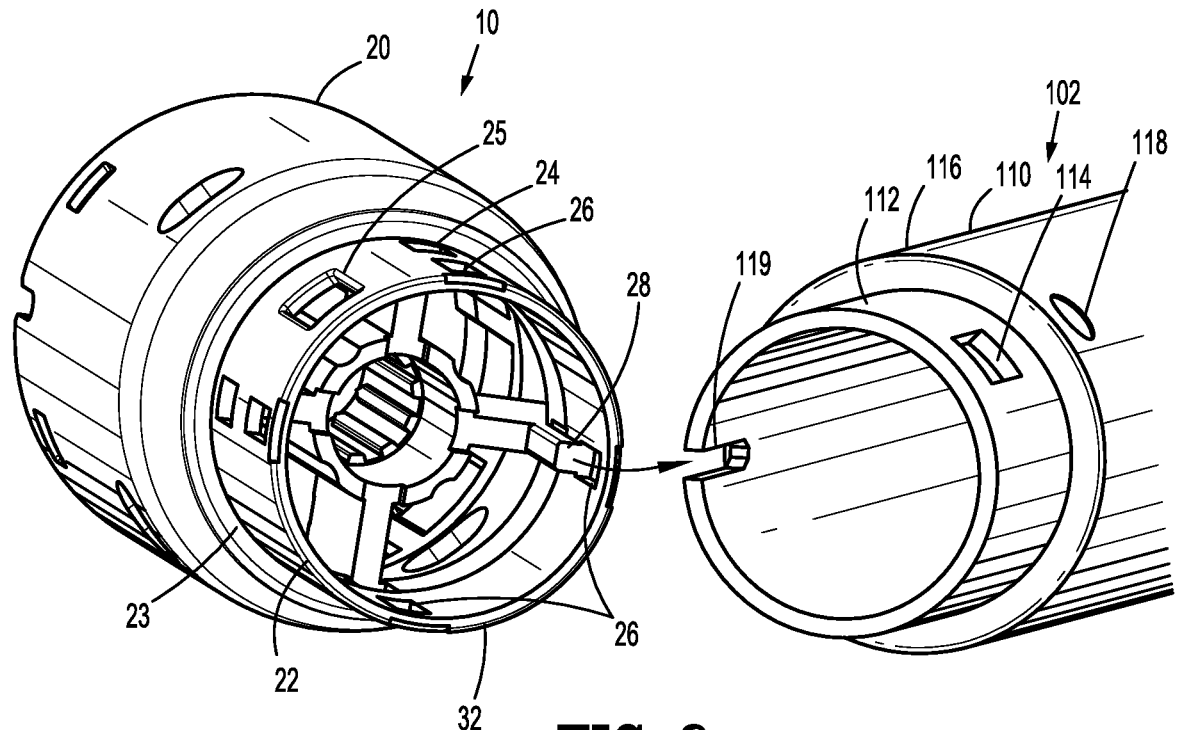
FIG. 6 is a perspective view of a shell assembly of the loading unit of FIG. 4 and a distal end portion of the adapter of FIG. 1.
Figure 7:
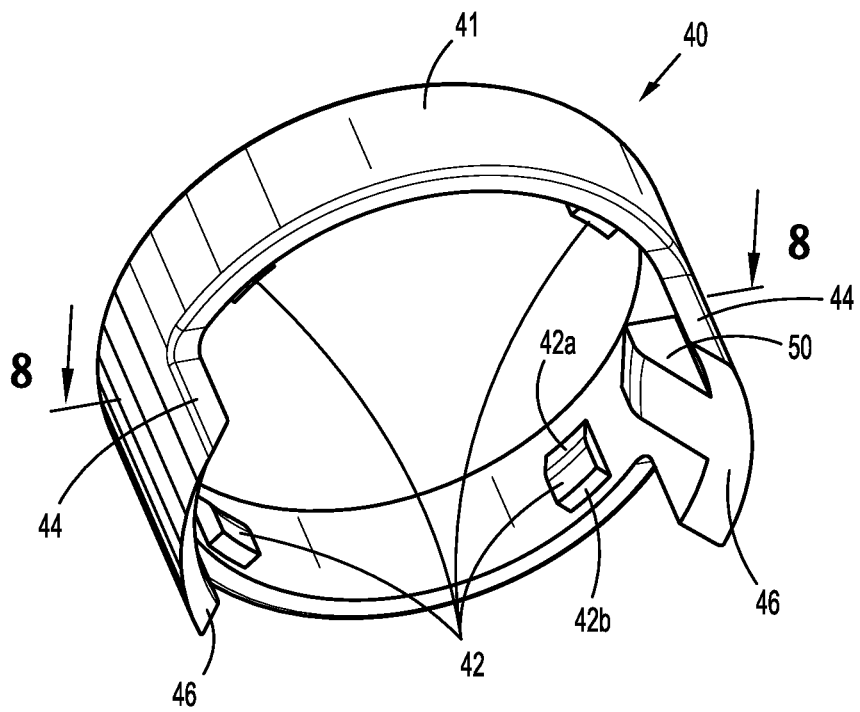
FIG. 7 is an enlarged perspective view of the lock collar of FIG. 5.
Figure 8:
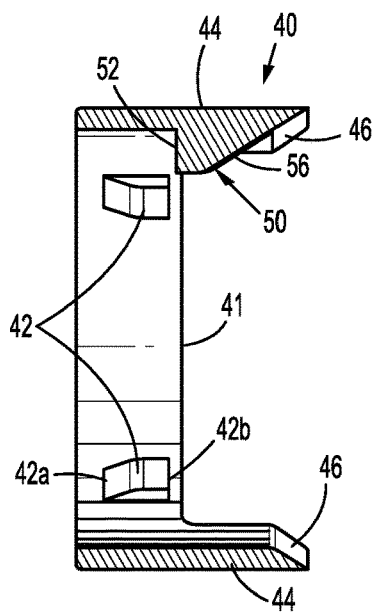
FIG. 8 is a cross-sectional view taken along section line 8-8 of FIG. 7.

With additional reference to FIG. 6, the coupling ring 22 of the shell assembly 20 includes a key 28 disposed on an inner surface of the coupling ring 22 extending in a direction parallel to a longitudinal axis of the shell assembly 20. As shown, the key 28 is aligned with one of the lock collar retention slots 24 and one of the release collar retention slots 26; however, it is contemplated that the key 28 may be positioned between two lock collar retention slots 24 and/or two release collar retention slots 26. However, the lock slot 25 and the key 28 may be adjacent one another or positioned anywhere about the coupling ring 22 relative to one another.

The mounting ring 112 of the adapter 102 defines the keyway 119 that receives the key 28 of the coupling ring 22 to align the loading unit 10 with the adapter 102. The keyway 119 extends in a direction that is parallel to a longitudinal axis of the distal end portion 110 of the adapter 102 and is sized to receive the key 28.

Referring to FIGS. 5-8, the lock collar 40 includes a lock ring 41 that includes lock collar retention tabs 42 and locking flanges 44. In embodiments, the lock collar retention tabs 42 extend inward from the lock ring 41, are substantially rectangular in shape, and are disposed about the lock ring 41. As shown, the lock collar retention tabs 42 are uniformly spaced about the lock ring 41 (i.e., at 90° apart); however, it is contemplated that the lock collar retention tabs 42 may assume a variety of configurations and may be non-uniformly spaced about the lock ring 41 to orientate the lock collar 40 with the coupling ring 22. It is envisioned that the lock ring 41 can include greater than or less than four lock collar retention tabs 42. The lock collar retention tabs 42 are sized to be received within a respective lock collar retention slot 24 of the coupling ring 22 and may be dimensioned to pass through inner and outer surfaces of the coupling ring 22.

The lock collar retention tabs 42 each include a cam surface 42a that is angled proximally inward and a proximal locking surface 42b that is substantially orthogonal to the longitudinal axis of the coupling ring 22 when the lock collar 40 is disposed about the coupling ring 22. The proximal locking surfaces 42b engage the coupling ring 22 when the lock collar retention tabs 42 are received within the lock collar retention slots 24 to prevent the lock collar 40 from moving proximally relative to the coupling ring 22.

The locking flanges 44 extend proximally from the lock ring 41. As shown, the lock ring 41 includes two locking flanges 44 that are diametrically opposed to one another. Each of the locking flanges 44 includes a tapered proximal cam surface 46 that is angled distally inward such that an outer surface of each locking flange 44 extends proximally beyond an inner surface of the locking flange 44.

One of the locking flanges 44 includes a lock 50 that extends inward from the inner surface of the locking flange 44. The lock 50 is sized and dimensioned to extend through the lock slot 25 of the coupling ring 22 and into the locking window 114 of the mounting ring 112 of the adapter 102 when the mounting ring 112 is received within the coupling ring 22 to secure the shell assembly 20 to the adapter 102. The lock 50 includes a locking surface 52 (FIG. 8) and a tapered cam surface 56 that is substantially aligned with the proximal cam surface 46. The locking surface 52 is substantially orthogonal to the longitudinal axis of the coupling ring 22 when the lock collar 40 is disposed about the coupling ring 22. The locking surface 52 engages a portion of the mounting ring 112 of the adapter 102 to secure the mounting ring 112 within the coupling ring 22 as detailed below. As shown, the cam surface 56 is angled distally inward and is congruent with the cam surface 46 of the locking flange 44. However, it is contemplated that the cam surface 56 may be disposed at a greater or lesser angle than the cam surface 46. The locking flanges 44 are constructed from a resilient material and are positioned such that the locking flanges 44 engage an outer surface of the coupling ring 22.

Figure 9:
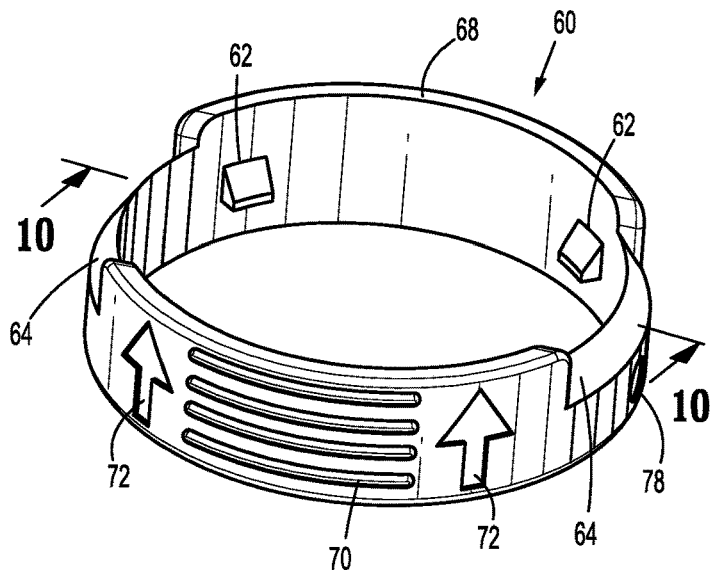
FIG. 9 is a perspective view of the release collar of FIG. 5.
Figure 10:
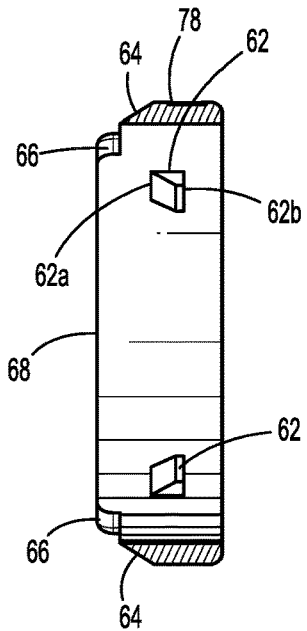
FIG. 10 is a cross-sectional view taken along section line 10-10 of FIG. 9.

Referring also to FIGS. 9 and 10, the release collar 60 includes release collar retention tabs 62 and cams 64. In embodiments, the release collar retention tabs 62 extend inward from an inner wall of the release collar 60, are substantially rectangular in shape, and are disposed about the release collar 60. As shown, the release collar retention tabs 62 are uniformly spaced about the release collar 60 (e.g., at 90° apart); however, it is contemplated that the release collar retention tabs 62 may assume a variety of configurations and be non-uniformly spaced about the release collar 60 to properly orient the release collar 60 in relation to the coupling ring 22. It is envisioned that the release collar 60 can include greater than or less than four release collar retention tabs 62. Each release collar retention tabs 62 is sized to be slidably received within a respective release collar retention slot 26 of the coupling ring 22 and may pass through inner and outer surfaces of the coupling ring 22. The release collar retention tabs 62 each include a cam surface 62a (FIG. 10) that is angled inwardly in a proximal direction and a proximal locking surface 62b that is substantially orthogonal to the longitudinal axis of the coupling ring 22 when the release collar 60 is disposed about the coupling ring 22. The proximal locking surfaces 62b engage the coupling ring 22 when the release collar retention tabs 62 are received within the release collar retention slots 26 to prevent the release collar 60 from sliding proximally relative to the coupling ring 22.

The release collar 60 also includes engagement features 70, actuation indicators 72, and an alignment indicator 78 (FIG. 9). As shown, the engagement features 70 include a plurality of radial ribs positioned or formed on an outside surface of the release collar 60; however, the engagement features 70 can include a textured surface or other suitable features for promoting engagement of the release collar 60 with the fingers of a clinician or a robotic mechanism to actuate the release collar 60 as detailed below. The actuation indicators 72 provide an indication as to the direction of movement required to actuate the release collar 60 to release the loading unit 10 as described in detail below. As shown, the actuation indicators 72 include arrows that are positioned or formed on the outer surface of the release collar 60.

The alignment indicator 78 is aligned with the lock 50 of the lock collar 40 when the release collar 60 is secured to the coupling ring 22 of the shell assembly 20 to provide visual and/or tactile indicia of the radial position of the lock 50. As shown, the alignment indicator 78 includes a circular depression in the outer surface of the release collar 60; however, the alignment indicator 78 can include textured, printed, raised, or identifiable indicia for providing visual and/or tactile identification of the radial position of the lock 50.

Figure 11:
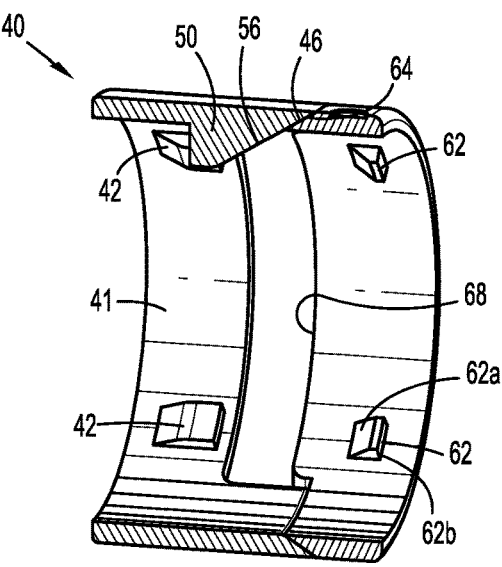
FIG. 11 is a cross-sectional view of the lock collar of FIG. 8 engaged with the release collar of FIG. 10 in a locked configuration.
Figure 17:
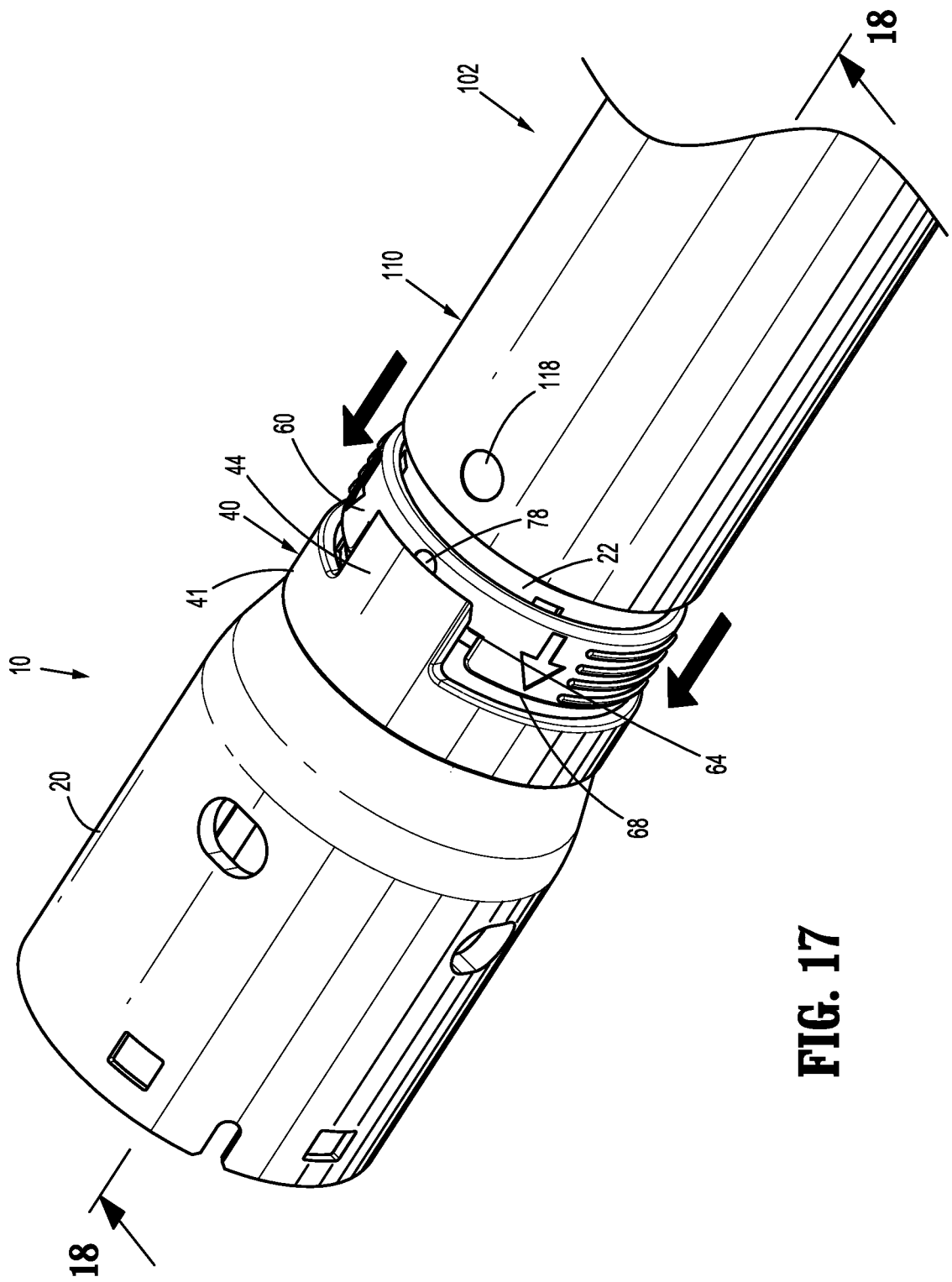
FIG. 17 is a perspective view of the loading unit and the distal end portion of the adapter of FIG. 3 with the release collar in an actuated position and the lock collar in an unlocked configuration.

As detailed above and described in greater detail below, the release collar retention tabs 62 of the release collar 60 are received within the release collar retention slots 26 of the coupling ring 22 of the shell assembly 20 such that the release collar 60 is slidable in a direction that is parallel to the longitudinal axis of the shell assembly 20 between a proximal unactuated position (FIG. 3) and a distal fully actuated position (FIG. 17). Movement of the release collar 60 between the distal actuated position and the proximal unactuated position transitions the lock collar 40 between the locked and unlocked configurations. With additional reference to FIG. 11, camming surfaces 64 of the release collar 60 are angled proximally outward to oppose and engage the cam surfaces 46 of the locking flanges 44 of the lock collar 40 when the release collar 60 is slid into engagement with the lock collar 40. Distal movement of the release collar 60 in relation to the lock collar 40 transitions the lock collar 40 from the unlocked to the locked configuration as detailed below. The stop surfaces 68 are positioned distal of the cam surfaces 64 such that in the unactuated position of the release collar 60, the stop surfaces 68 define a gap with the lock ring 41 and in a fully actuated position of the release collar 60, the stop surfaces 68 are engaged with the lock ring 41.

With reference to FIGS. 12-16, a method of coupling a loading unit 10 to an adapter 102, or surgical instrument, is described in accordance with the present disclosure. Initially referring to FIG. 12, the loading unit 10 is aligned with the distal end portion 110 of the adapter 102 such that the longitudinal axes of each are coincident with one another. In addition, the loading unit 10 is radially aligned or indexed with the distal end portion 110 by rotating the loading unit 10 until the alignment indicator 78 of the release collar 60 is aligned with an alignment indicator 118 of the distal end portion 110 of the adapter 102. When the alignment indicators 78, 118 are aligned with one another, this indicates that the key 24 is aligned with the keyway 119 and the lock 50 is aligned with the lock slot 25. It is contemplated that the mounting ring 112 of the adapter 102 can be partially received within the cylindrical opening 21 of the coupling ring 22 during alignment of the loading unit 10 with the adapter 102.

Figure 13:
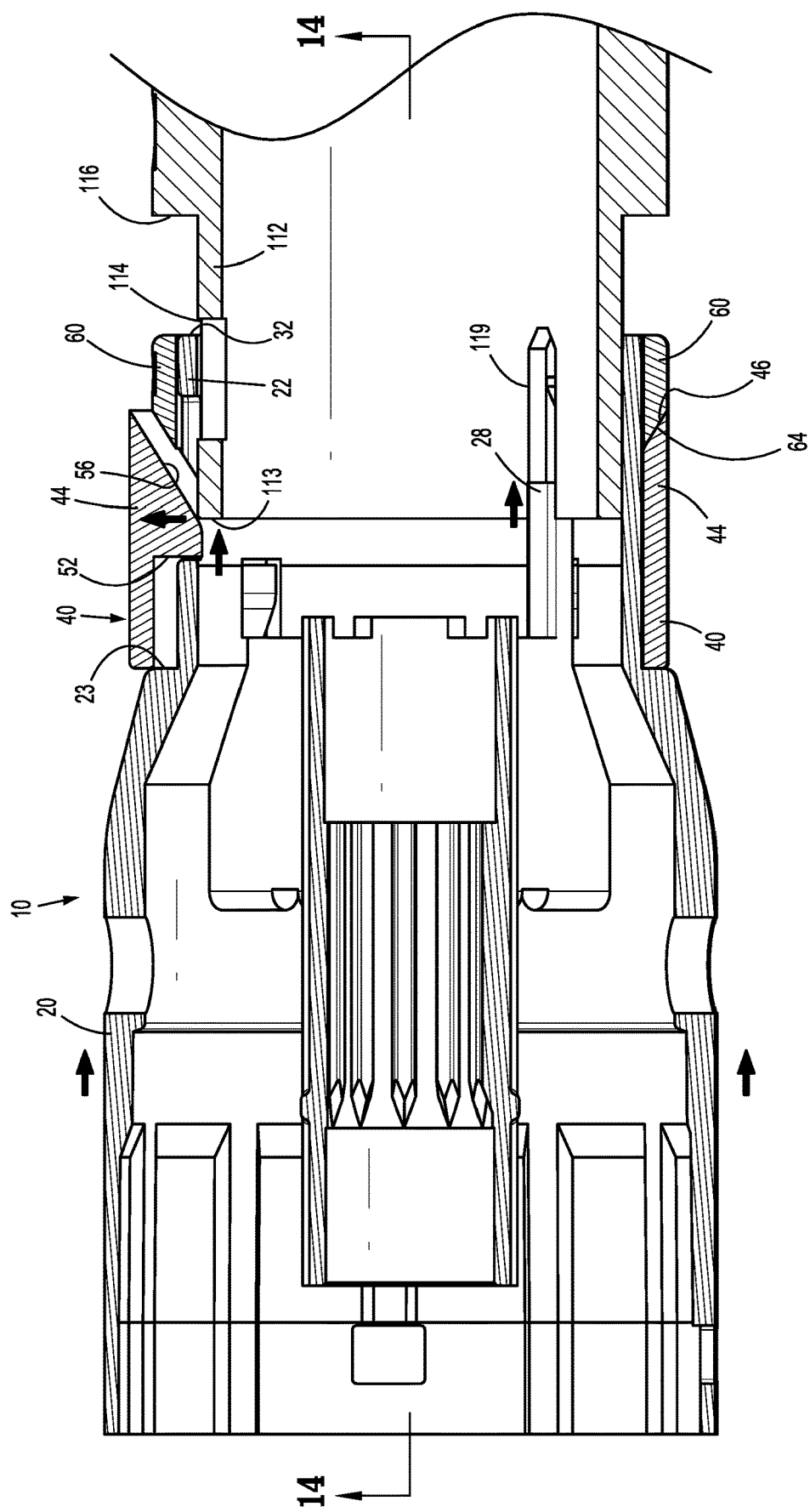
FIG. 13 is a cross-sectional view of the loading unit of FIG. 12 partially slid over the distal end portion of the adapter with the lock collar in an unlocked configuration and the release collar in an unactuated position.
Figure 15:
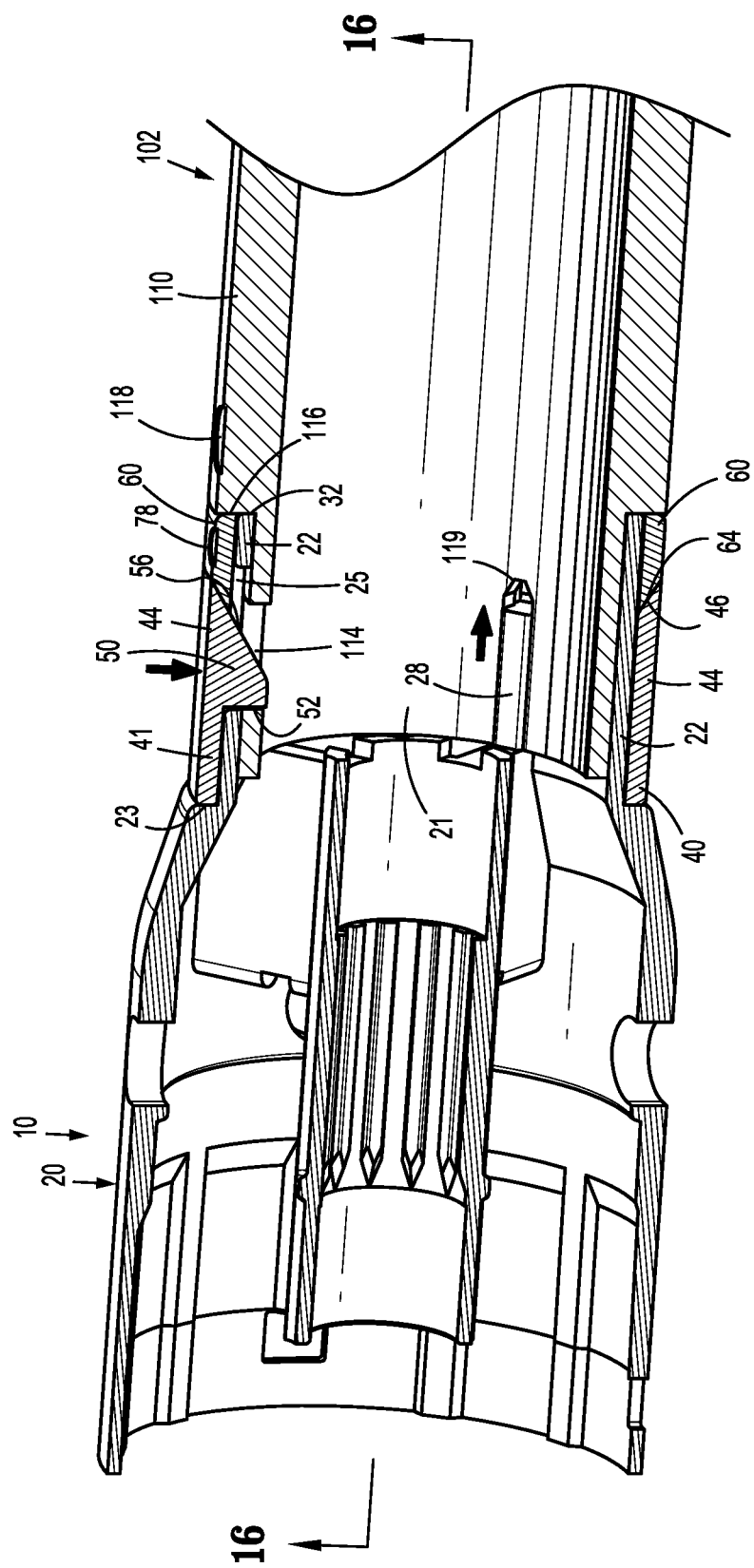
FIG. 15 is a cross-sectional view of the loading unit of FIG. 13 secured onto the distal end portion of the adapter with the lock collar in the locked configuration and release collar in an unactuated position.
Figure 16:
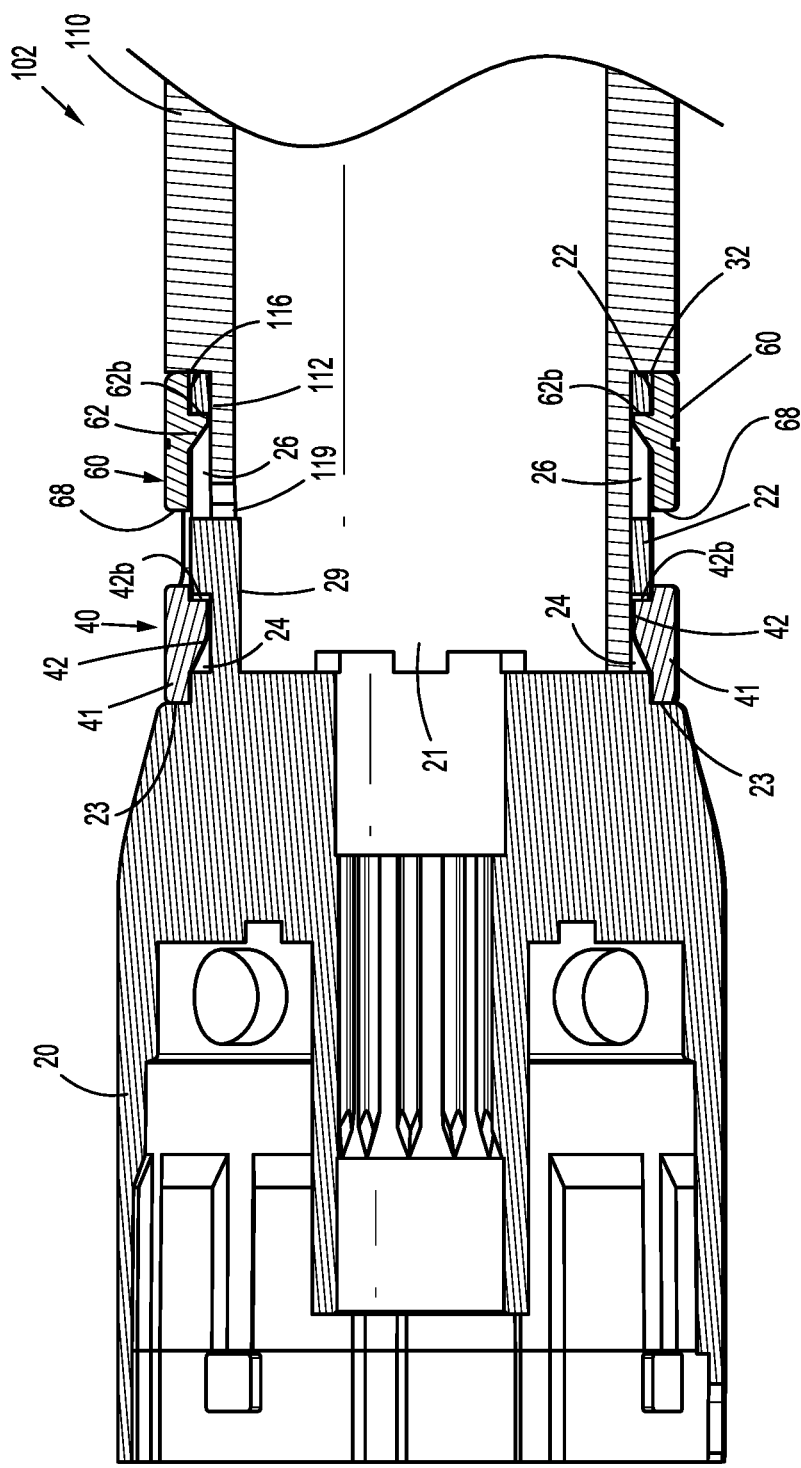
FIG. 16 is a cross-sectional view taken along section line 16-16 of FIG. 15.

When the loading unit 10 is radially aligned with the distal end portion 110 of the adapter 102, the loading unit 10 can be mounted on the mounting ring 112 of the adapter 102. Specifically, the loading unit 10 can be slid proximally over the mounting ring 112 of the adapter 102 until the proximal end 32 of the shell assembly 20 abuts the shoulder 116 of the distal end portion 110 of the adapter 102 as shown in FIGS. 15 and 16. As the loading unit 10 is slid over the mounting ring 112 in the direction indicated by arrows "A" in FIG. 13, the distal end 113 of the distal end portion 110 of the adapter 102 engages the cam surface 56 of the lock 50 of the lock collar 40 that extends through the lock slot 25 of the coupling ring 22 as shown in FIG. 13. Engagement between the distal end 113 and the cam surface 56 of the lock 50 urges or cams the lock 50 outward of the cylindrical opening 21 of the coupling ring 22, in the direction indicated by arrow "B" in FIG. 13, to the unlocked configuration.

Figure 14:
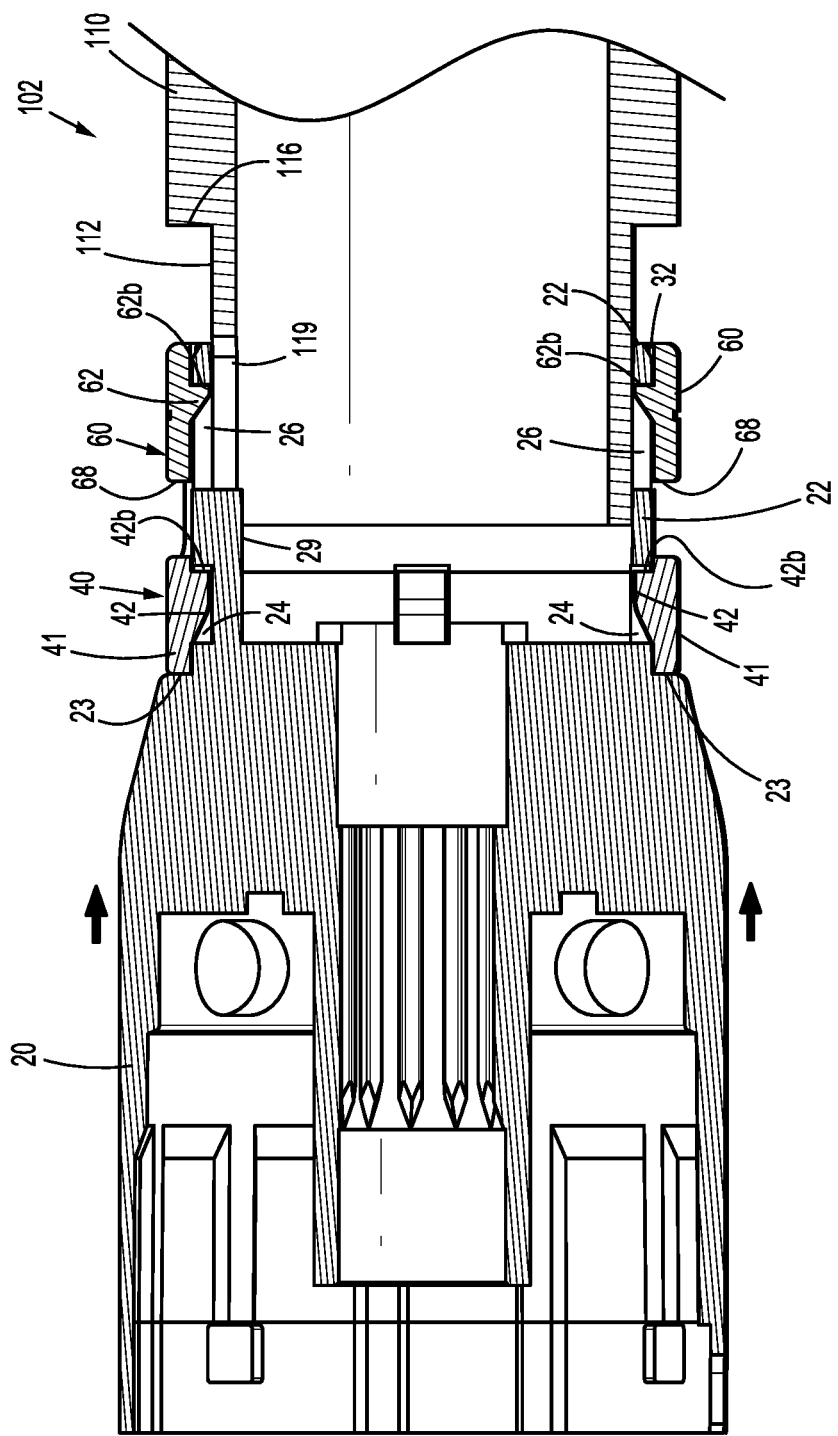
FIG. 14 is a cross-sectional view taken along section line 14-14 of FIG. 13.

As the distal end 113 of the adapter 102 cams the lock 50 out of the cylindrical opening 21 of the coupling ring 22, the lock collar 40 maintains the release collar 60 in the unactuated position. Specifically, the cam surface 46 of the opposing locking flange 44 maintains engagement with the camming surface 64 of the release collar 60 such that the lock collar 40 maintains the release collar 60 in the unactuated position. As shown in FIG. 14, the locking ring 41 abuts the step 23 of the shell assembly 20 to prevent distal translation of the lock collar 40. In addition, the lock collar retention tabs 42 are disposed within the lock collar retention slots 24 of the coupling ring 22 with the locking surfaces 42b engaged with the coupling ring 22 to prevent proximal translation of the lock collar 40. Further, the release collar retention tabs 62 are disposed within the release collar retention slots 26 with the locking surfaces 62b engaged with the coupling ring 22 to prevent proximal translation of the release collar 60.

With particular reference to FIGS. 15 and 16, when the proximal end 32 of the shell assembly 20 abuts the shoulder 116 of the adapter 102, or surgical instrument, the lock collar 40 is in the locked configuration with the lock 50 passing through the lock slot 25 of the coupling ring 22 and into the locking window 114 of the mounting ring 112 to secure the loading unit 10 to the adapter 102. Specifically, the locking surface 52 of the lock 50 engages the mounting ring 112 between the locking window 114 and the distal end 113 to prevent the mounting ring 112 from withdrawing from within the cylindrical opening 21 of the shell assembly 20. When the lock collar 40 reaches the locked configuration, the lock 50 may be configured to provide audible indicia (e.g., a click) to a user that the lock collar 40 is in the locked configuration.

When the lock collar 40 is in the locked configuration, the cam surfaces 46 of the locking flanges 44 maintain engagement with the camming surfaces 64 of the release collar 60 such that the lock collar 40 maintains the release collar 60 in the unactuated position. As shown in FIG. 16, the locking ring 41 abuts the step 23 of the shell assembly 20 to prevent distal translation of the lock collar 40. In addition, the lock collar retention tabs 42 are disposed within the lock collar retention slots 24 of the coupling ring 22 with the locking surfaces 42b engaged with the coupling ring 22 to prevent proximal translation of the lock collar 40. Further, the release collar retention tabs 62 are disposed within the release collar retention slots 26 with the locking surfaces 62b engaged with the coupling ring 22 to prevent proximal translation of the release collar 60.

With the loading unit 10 secured to the distal end portion 110 of the adapter 102, the surgical instrument and loading unit 10 may be used to perform a surgical procedure. After surgical procedure is completed, the loading unit 10 can be decoupled or detached from the surgical instrument as will be described in detail below. With the loading unit 10 decoupled from the surgical instrument, another loading unit may be coupled or secured to the surgical instrument for continued use in the surgical procedure, the surgical instrument may be sterilized for use in another surgical procedure, or the surgical instrument may be discarded. In addition, the loading unit 10 may be sterilized for use in another surgical procedure or may be discarded.

Figure 18:
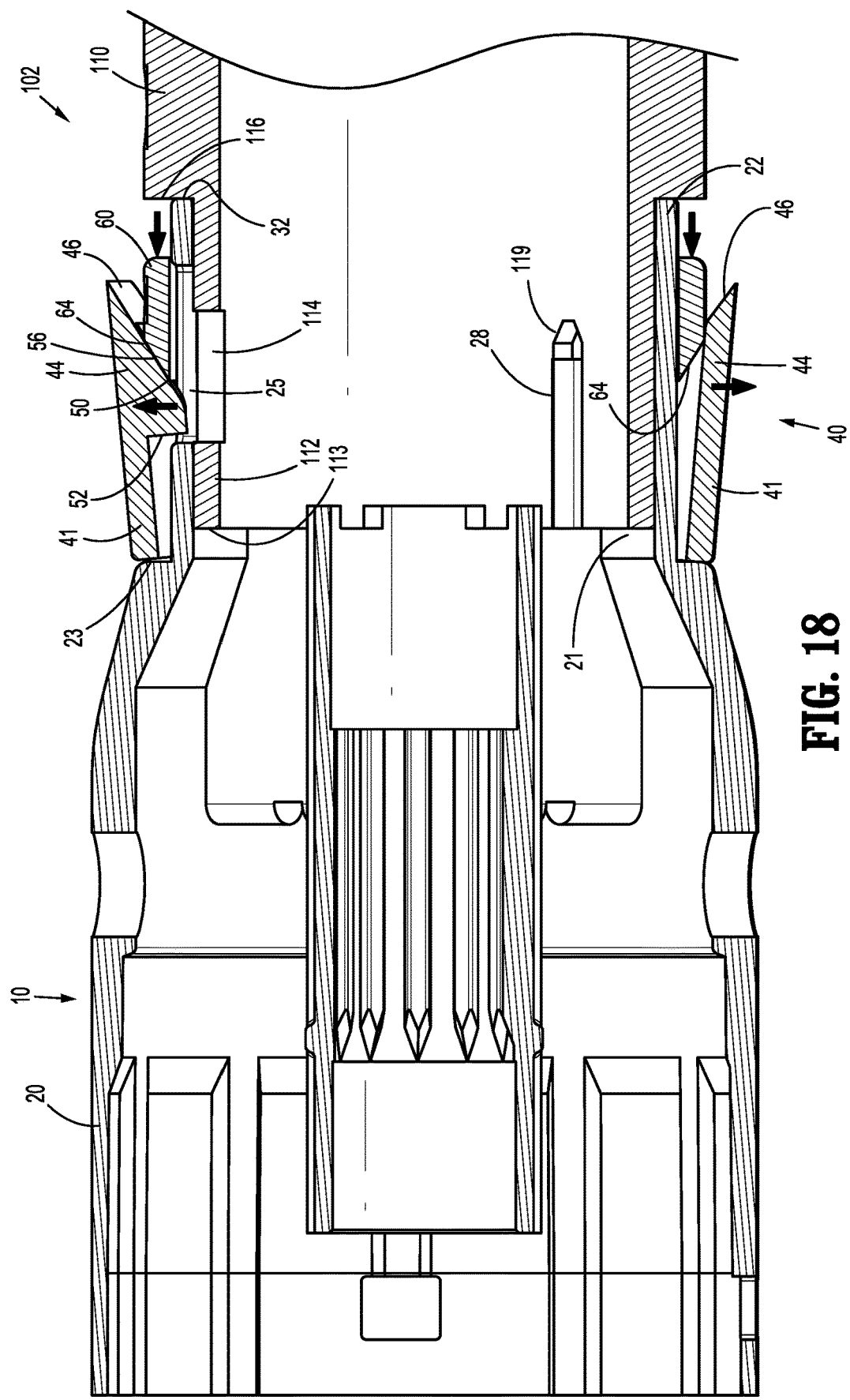
FIG. 18 is a cross-sectional view taken along section line 18-18 of FIG. 17.

With reference to FIGS. 17-20, a method of removing the loading unit 10 from the adapter 102, or surgical instrument, is described in accordance with the present disclosure. Initially, the release collar 60 is actuated or translated distally from the unactuated position to the actuated position as shown in FIGS. 17 and 18. A clinician can engage the engagement features 70 of the release collar 60 to distally translate the release collar 60. As the release collar 60 is translated towards the actuated position, the camming surface 64 slides against the cam surfaces 46 of the locking flanges 44 and the cam surface 56 of the lock to lift 50 of the lock collar 40 to an unlocked configuration such that the lock 50 is outside of the locking window 114 of the mounting ring 112 and can be outside of the lock slot 25 of the coupling ring 22. It will be appreciated that when the release collar 60 is translated to the actuated position, the release collar 60 lifts both locking flanges 44 of the lock collar 40.

Figure 19:
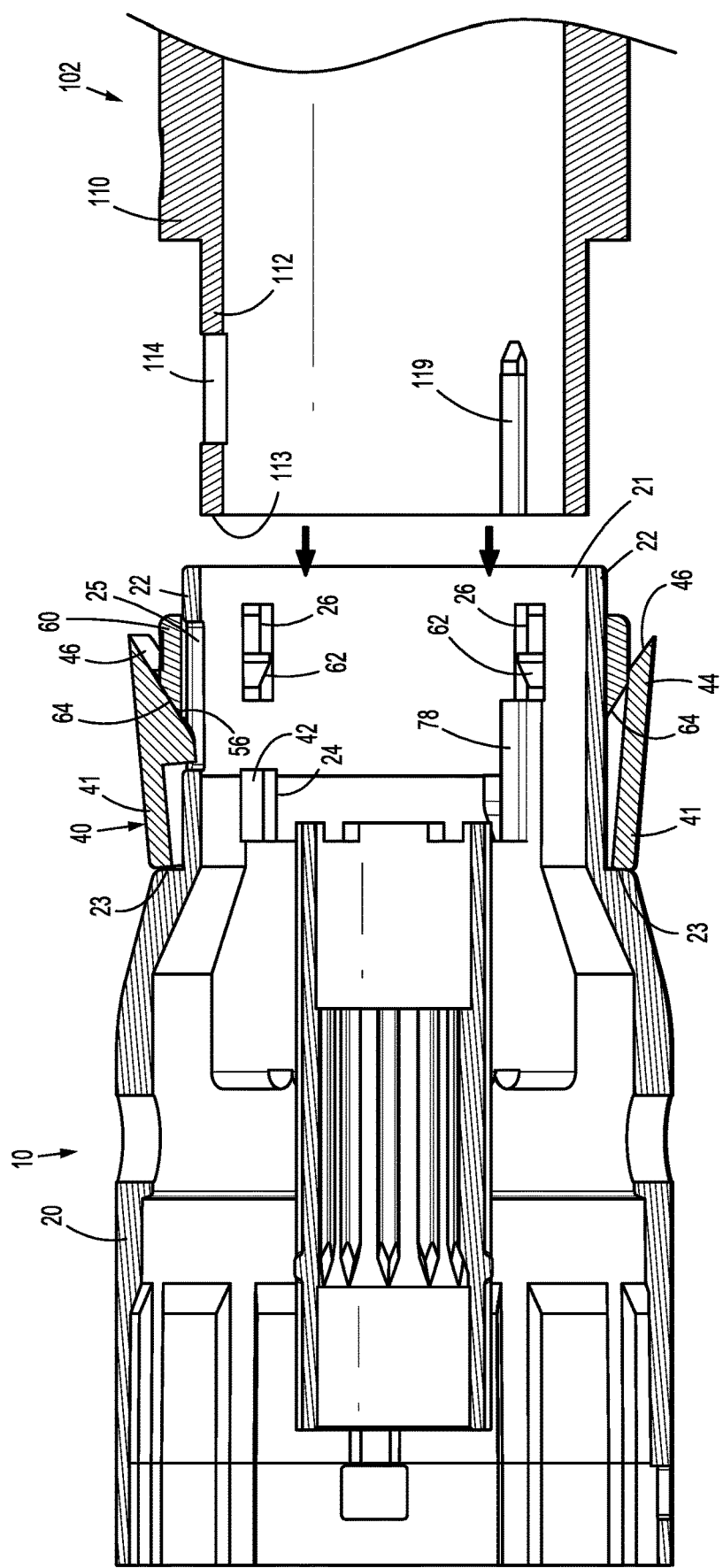
FIG. 19 is a cross-sectional view of the loading unit and the distal end portion of the adapter of FIG. 18 with the loading unit slid off of the distal end portion of the adapter.

When the lock 50 is lifted out of the locking window 114, the locking ring 41 engages the step 23 of the shell assembly 20 to slide the shell assembly 20 distally off of the mounting ring 112 of the adapter 102 as shown in FIG. 19. In addition, the stop surfaces 68 (FIG. 9) can engage the locking ring 41 which engages the step 23 to remove the loading unit 10 from the adapter 102. As shown in FIG. 19, when the release collar 60 is translated to the actuated position, the release collar retention tabs 62 slide distally within the release collar retention slots 26.

Figure 20:
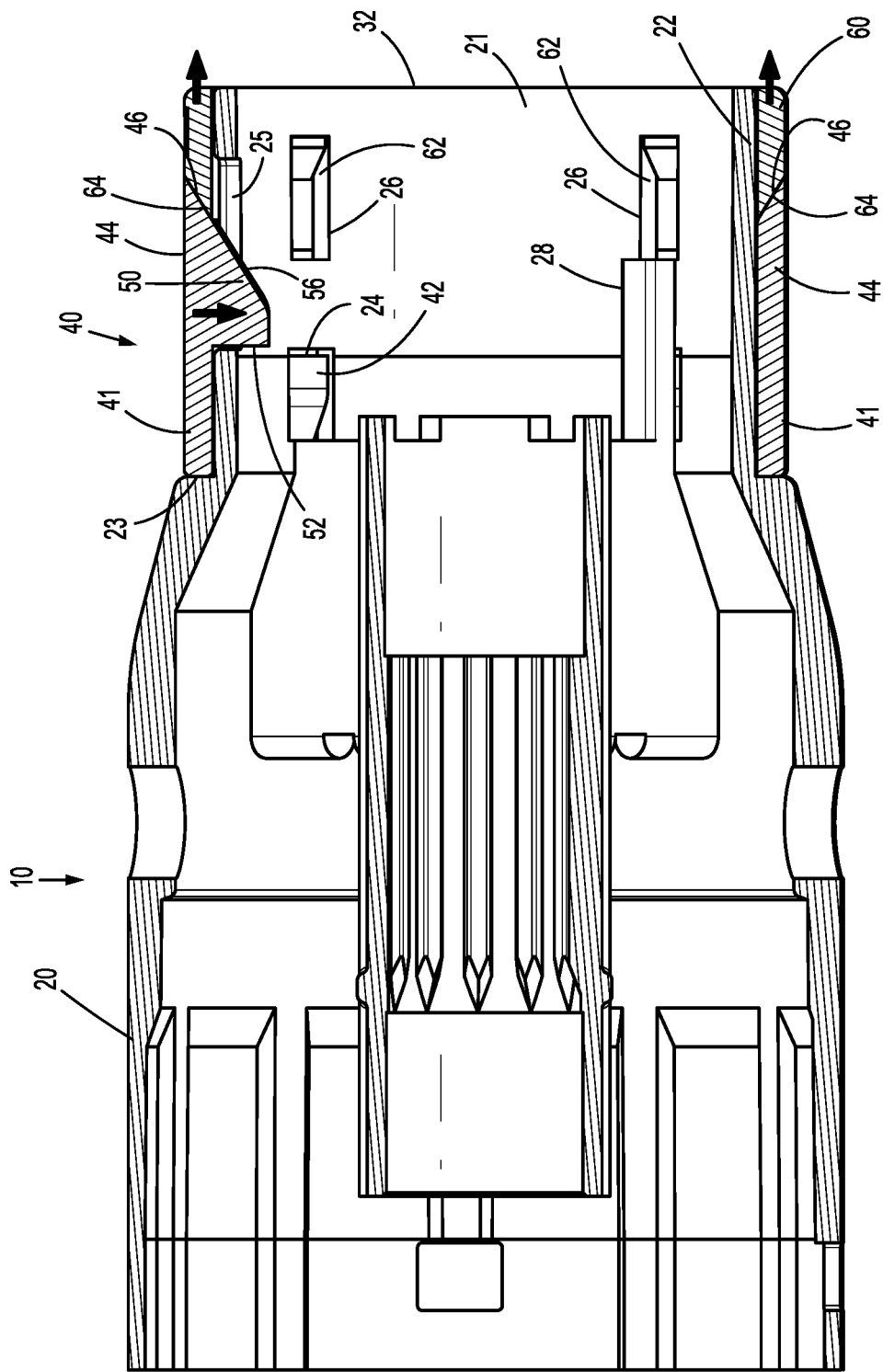
FIG. 20 is a cross-sectional view of the loading unit of FIG. 19 with the release collar released and urged to the unactuated position by engagement of the lock collar.

Referring to FIG. 20, when the loading unit 10 is removed from adapter 102, the release collar 60 is released. When the release collar 60 is released, resilience of the locking flanges 44 urge the locking flanges 44 inward. As the locking flanges 44 move inward, the cam surfaces 46 of the locking flanges 44 and/or the cam surface 56 of the lock 52 engage the camming surfaces 64 of the release collar 60 to proximally translate the release collar 60 to the unactuated position. When the release collar 60 reaches the unactuated position, the lock collar 40 is in the locked configuration with lock 50 passing through the lock slot 25.

As detailed above, the locking flanges 44 of the lock collar 40 are made of a resilient material. For example, the locking flanges 44 may be formed of a resilient plastic material using an injection molding process. However, it is contemplated the locking flanges 44 may be formed of other suitable materials including, but not limited to, spring steel, stainless steel, or wire.

While several embodiments of the disclosure have been shown in the drawings, it is not intended that the disclosure be limited thereto, as it is intended that the disclosure be as broad in scope as the art will allow and that the specification be read likewise. Any combination of the above embodiments is also envisioned and is within the scope of the appended claims. The present disclosure is not limited to circular stapling loading units, but has application to loading units for linear stapling or other types of instruments, such as electrocautery or ultrasonic instruments. Therefore, the above description should not be construed as limiting, but merely as exemplifications of particular embodiments. Those skilled in the art will envision other modifications within the scope of the claims appended hereto.

What is claimed:

1. A loading unit comprising:
   a shell assembly having a coupling ring defining a proximal opening configured to receive a distal end portion of a surgical instrument, the coupling ring defining a lock slot;
   a lock collar disposed about the coupling ring, the lock collar including a radially extending lock configured to be received within the lock slot, the lock collar being transitionable between a locked configuration, in which the lock is positioned within the lock slot, and an unlocked configuration, in which the lock is lifted from within the lock slot, the lock collar configured to secure the loading unit to a surgical instrument in the locked configuration; and
   a release collar disposed about the coupling ring proximal of the lock collar, the release collar translatable between an unactuated position and an actuated position, the release collar transitioning the lock collar to the unlocked configuration as the release collar is distally translated from the unactuated position towards the actuated position.

2. The loading unit according to claim 1, wherein the lock collar includes a lock ring and a first resilient locking flange extending proximally from the lock ring, the first locking flange supporting the lock, the lock passing through the lock slot and into the proximal opening in the locked configuration and the lock positioned outside of the proximal opening in the unlocked configuration.

3. The loading unit according to claim 2, wherein the first locking flange includes a cam surface angled distally inward, wherein the release collar has a first camming surface angled proximally outward, and wherein in the locked configuration the cam surface of the first locking flange engages the first camming surface to urge the release collar towards the unactuated position.

4. The loading unit according to claim 3, wherein in the actuated position, the first camming surface engages the cam surface of the first locking flange to transition the lock collar to the unlocked configuration.

5. The loading unit according to claim 1, wherein the lock collar urges the release collar towards the unactuated position.

6. The loading unit according to claim 5, wherein the lock collar includes a second resilient locking flange extending proximally from the lock ring and opposes the first locking flange.

7. The loading unit according to claim 6, wherein the second locking flange has a cam surface that is angled distally inward, wherein the release collar has a second camming surface that is angled proximally outward, and wherein the cam surface of the second locking flange engages the second camming surface of the release collar to urge the release collar towards the unactuated position.

8. The loading unit according to claim 7, wherein in the actuated position of the release collar, the second camming surface lifts the second locking flange away from the coupling ring.

9. The loading unit according to claim 1, wherein the coupling ring defines a plurality of lock collar retention slots, wherein the lock collar includes a plurality of lock collar retention tabs, and wherein each of the retention tabs is received within a respective lock collar retention slot to secure the lock collar to the coupling ring.

10. The loading unit according to claim 1, wherein the coupling ring defines a plurality of release collar retention slots, wherein the release collar includes a plurality of release collar retention tabs, and wherein each of the retention tabs is slidably received within a respective release collar retention slot to retain the release collar about the coupling ring.

11. A surgical system comprising:
    a surgical instrument including a distal end portion that defines a locking window;
    a loading unit including a shell assembly having a coupling ring defining a proximal opening that receives the distal end portion, the coupling ring defining a lock slot;
    a lock collar disposed about the coupling ring, the lock collar including a radially extending lock configured to be received within the lock slot, the lock collar being transitionable between a locked configuration, in which the lock is positioned within the lock slot, and an unlocked configuration, in which the lock is lifted from within the lock slot, the lock collar configured to secure the loading unit to the distal end portion of the surgical instrument in the locked configuration; and
    a release collar disposed about the coupling ring proximal of the lock collar, the release collar translatable between an unactuated position and an actuated position, the release collar transitioning the lock collar to the unlocked configuration as the release collar is distally translated from the unactuated position toward the actuated position.

12. The surgical system according to claim 11, wherein the coupling ring includes a key extending into the proximal opening, and wherein the distal end portion of the surgical instrument defines a keyway, the key parallel to a longitudinal axis of the shell assembly, the keyway parallel to a longitudinal axis of the distal end portion of the surgical instrument, the key received within the keyway to rotatably fix the loading unit to the distal end portion of the surgical instrument.

13. The surgical system according to claim 11, wherein the lock collar includes a lock ring and a first resilient locking flange extending proximally from the lock ring, the first locking flange supporting the lock, the lock including a cam surface angled distally inward, a distal end of the surgical instrument configured to engage the cam surface of the lock to transition the lock collar to the unlocked configuration as the distal end portion of the surgical instrument is received within the proximal opening until the locking window is aligned with the lock slot of the coupling ring.

14. The surgical system according to claim 11, wherein the release collar includes alignment indicia and the distal end portion of the surgical instrument includes an alignment indicator, wherein when the distal end portion is received within the proximal opening, the alignment indicia of the release collar and the alignment indicator of the distal end portion are aligned with one another to align a lock of the lock collar with the locking window of the distal end portion.

15. A method of securing a loading unit to a surgical instrument, comprising:
aligning a coupling ring of the loading unit with a distal end portion of the surgical instrument;
sliding the coupling ring over the distal end portion of the surgical instrument, a distal end of the surgical instrument engaging a lock of a lock collar disposed over the coupling ring to lift the lock, the lock supported on a first locking flange of the lock collar, the lock collar including a second locking flange opposing the first locking flange, the second locking flange engaging a release collar disposed about the coupling ring proximal of the lock collar to urge the release collar proximally; and
continuing to slide the loading unit over the distal end portion until a locking window defined in the distal end portion of the surgical instrument is aligned with the lock such that resilience of the first locking flange moves the lock into the locking window to secure the loading unit to the surgical instrument.

16. The method according to claim 15, further comprising releasing the loading unit from the distal end portion of the surgical instrument including:

actuating the release collar distally along the coupling ring to lift the lock from within the locking window; and
sliding the loading unit off of the distal end portion of the surgical instrument.

17. The method according to claim 16, wherein actuating the release collar distally includes engaging a cam surface of the first locking flange with a first camming surface of the release collar to lift the lock from within the locking window.

18. The method according to claim 17, further comprising releasing the release collar after sliding the loading unit off of the distal end portion of the surgical instrument such that the cam surface engages the first camming surface to urge the release collar proximally along the coupling ring in response to resilience of the first locking flange.

19. The method according to claim 17, wherein actuating the release collar distally includes engaging a cam surface of the second locking flange with a second camming surface of the release collar to lift the second locking flange.

20. The method according to claim 16, wherein aligning the coupling ring of the loading unit with the distal end portion of the surgical instrument includes aligning alignment indicia of the release collar with an alignment indicator of the distal end portion.

* * * * *